United States Patent [19]
Dobak, III et al.

[11] Patent Number: 6,035,657
[45] Date of Patent: *Mar. 14, 2000

[54] FLEXIBLE CATHETER CRYOSURGICAL SYSTEM

[75] Inventors: John D. Dobak, III, La Jolla, Calif.;
Ray Radebaugh, Louisville, Colo.;
Eric Marquardt, Lakewood, Colo.

[73] Assignees: CryoGen, Inc., San Diego, Calif.;
Secretary of Commerce, Washington, D.C.

[*] Notice: This patent is subject to a terminal disclaimer.

[21] Appl. No.: 09/287,669

[22] Filed: Apr. 7, 1999

Related U.S. Application Data

[60] Division of application No. 08/895,681, Jul. 17, 1997, which is a continuation-in-part of application No. 08/542,123, Oct. 12, 1995.

[51] Int. Cl.$^7$ ........................................................ F25D 3/00
[52] U.S. Cl. ............................. 62/293; 62/50.7; 62/51.2; 165/81; 165/164; 606/21
[58] Field of Search .................... 165/164, 80.4, 165/81; 62/51.2, 50.7, 293; 606/21

[56] References Cited

U.S. PATENT DOCUMENTS

| | | | |
|---|---|---|---|
| 3,534,813 | 10/1970 | Fleming | 165/164 |
| 4,494,171 | 1/1985 | Bland et al. | 361/704 |
| 4,559,580 | 12/1985 | Lutfy | 165/80.4 X |
| 5,058,665 | 10/1991 | Harada | 165/164 |
| 5,101,894 | 4/1992 | Hendricks | 165/164 |
| 5,139,496 | 8/1992 | Hed | 606/23 |
| 5,337,572 | 8/1994 | Longsworth | 62/51.2 |
| 5,365,750 | 11/1994 | Greenthal | 62/293 |
| 5,759,182 | 6/1998 | Varney et al. | 606/21 |

*Primary Examiner*—Ronald Capossela
*Attorney, Agent, or Firm*—Gerald W. Spinks

[57] ABSTRACT

A microminiature laminated heat exchanger for use in a cryogenic probe, and a method of manufacture. The heat exchanger has high and low pressure flow patterns etched into oxygen free copper sheets, with the flow patterns being tortuous paths promoting turbulent flow. The sheets containing the flow patterns are bonded into a laminated assembly in the shape of a cylinder, with a high pressure inlet and a low pressure outlet in a first end, and a high pressure outlet and a low pressure inlet in a second end. The high pressure flow path lies alongside the low pressure flow path, with flow in the two paths being in opposite directions, to accomplish counterflow heat exchange.

4 Claims, 18 Drawing Sheets

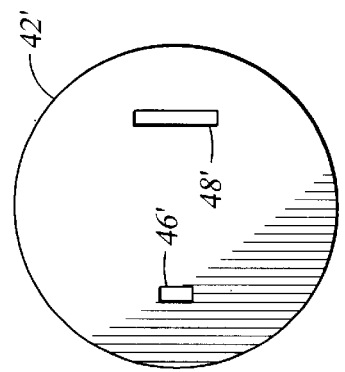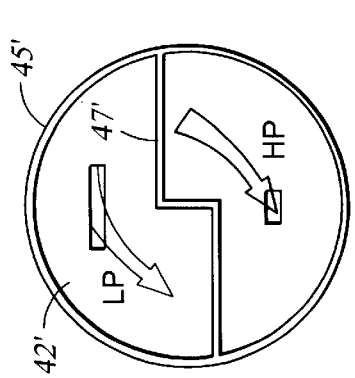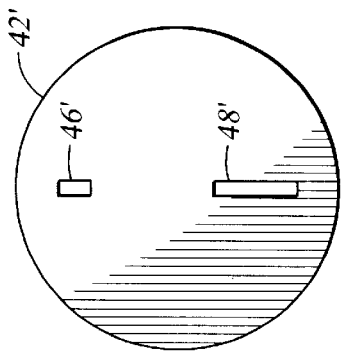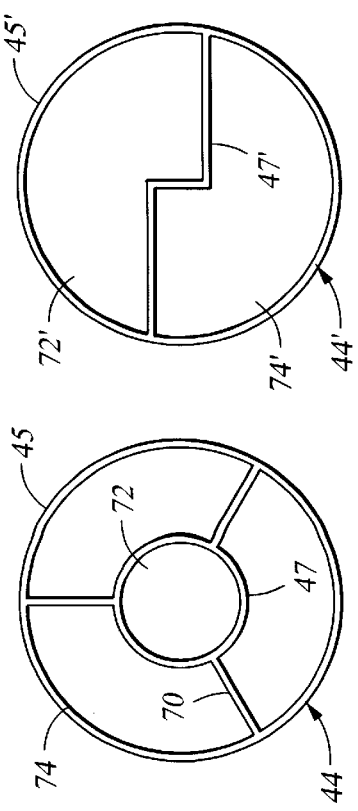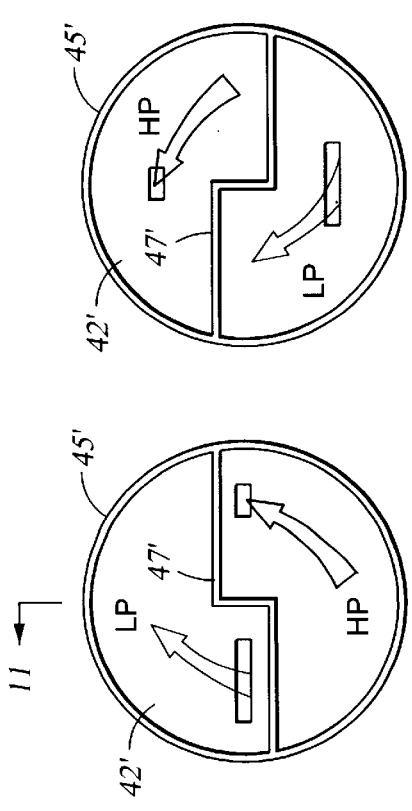

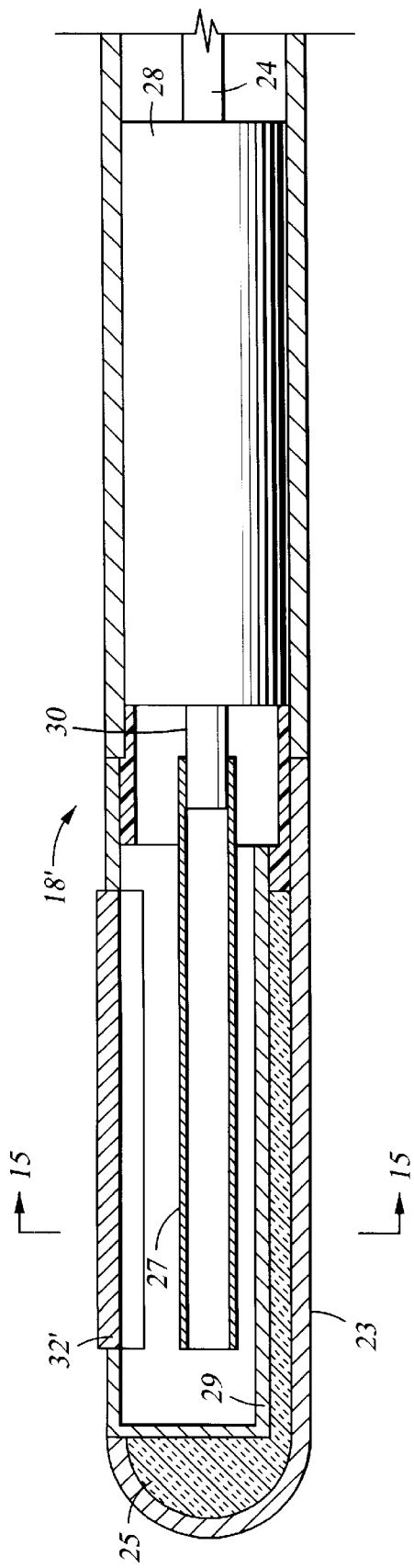
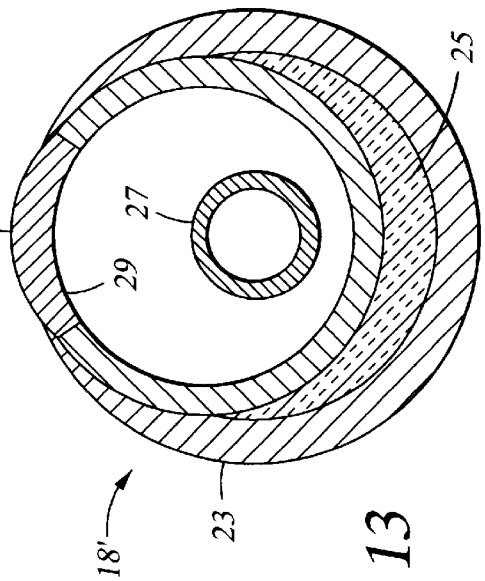
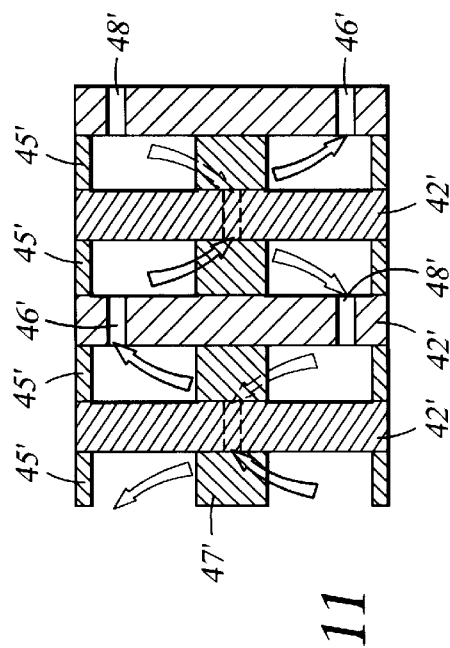
Fig. 12
Fig. 13
Fig. 11

FLEXIBLE CATHETER CRYOSURGICAL SYSTEM

CROSS REFERENCE TO RELATED APPLICATIONS

This is a continuation patent application of co-pending U.S. patent application Ser. No. 08/895,681, filed on Jul. 17, 1997, entitled "Cryogenic Heat Exchanger", which was a continuation-in-part application of co-pending U.S. patent application Ser. No. 08/542,123, filed on Oct. 12, 1995, entitled "Miniature Mixed Gas Refrigeration System".

STATEMENT REGARDING FEDERALLY SPONSORED RESEARCH OR DEVELOPMENT

The U.S. Government has a paid up license in this invention and the right to have this invention practiced on behalf of the Government, as provided for by the terms of Contract No. CRADA: CN-1090, awarded by the National Institute of Standards and Technology.

BACKGROUND OF THE INVENTION

1. Field of the Invention

This invention is in the field of cryosurgical apparatus used to cool very small portions of biological tissue to very low temperatures, by insertion of a small diameter, flexible catheter to the treatment area.

2. Background Information

In the field of medicine, it may be desirable to be able to cool miniature discrete portions of biological tissue to very low temperatures in the performance of cryosurgery, without substantially cooling adjacent tissues of the organ. While miniature refrigeration systems may have application in other fields, the present invention provides an apparatus which is uniquely suited for the field of miniature cryosurgery.

Cryosurgery has become an important procedure in medical, dental, and veterinary fields. Particular success has been experienced in the specialties of gynecology and dermatology. Other specialties, such as neurosurgery and urology, could also benefit from the implementation of cryosurgical techniques, but this has only occurred in a limited way. Unfortunately, currently known cryosurgical instruments have several limitations which make their use difficult or impossible in some such fields. Specifically, known systems are not optimally designed to have sufficient precision and flexibility to allow their widespread use endoscopically and percutaneously.

In the performance of cryosurgery, it is typical to use a cryosurgical application system designed to suitably freeze the target tissue, thereby destroying diseased or degenerated cells in the tissue. The abnormal cells to be destroyed are often surrounded by healthy tissue which must be left uninjured. The particular probe or other applicator used in a given application is therefore designed with the optimum shape and size for the application, to achieve this selective freezing of tissue. Where a probe is used, the remainder of the refrigeration system must be designed to provide adequate cooling, which involves lowering the operative portion of the probe to a desired temperature, and having sufficient power or capacity to maintain the desired temperature for a given heat load. The entire system must be designed to place the operative portion of the probe at the location of the tissue to be frozen, without having any undesirable effect on other organs or systems.

Currently known cryosurgical systems typically use liquid nitrogen or nitrous oxide as coolant fluids. Liquid nitrogen is usually either sprayed onto the tissue to be destroyed, or it is circulated to cool a probe which is applied to the tissue. Liquid nitrogen has an extremely low temperature of approximately 77 K, and a high cooling capacity, making it very desirable for this purpose. However, liquid nitrogen typically is allowed to evaporate and escape to the atmosphere during use, requiring the continual replacement of storage tanks. Further, since the liquid is so cold, the probes and other equipment used for its application require vacuum jackets or other types of insulation. This makes the probes relatively complex, bulky, and rigid, and therefore unsuitable for endoscopic or intravascular use. The need for relatively bulky supply hoses and the progressive cooling of all the related components make the liquid nitrogen instruments less than comfortable for the physician, as well, and they can cause undesired tissue damage.

A nitrous oxide system typically achieves cooling by pressurizing the gas and then expanding it through a Joule-Thomson expansion element, such as a valve, orifice, or other type of flow constriction, at the end of a probe tip. Any such device will be referred to hereinafter simply as an "expansion element". The typical nitrous oxide system pressurizes the gas to 700 to 800 psia., to reach practical temperatures of no lower than about 190 K to 210 K. Nitrous oxide systems are not able to approach the temperature and power achieved by the nitrogen systems. The maximum temperature drop that can be achieved in a nitrous oxide system is to 184 K, which is the boiling point of nitrous oxide. The nitrous oxide system does have some advantages, in that the inlet high pressure gas is essentially at room temperature until it reaches the Joule-Thomson element at the probe tip. This eliminates the need for insulation of the system, facilitating miniaturization and flexibility to some extent However, because of the relatively warm temperatures and low power, tissue destruction power is limited. For many such applications, temperatures below 184 K are desirable. Further, the nitrous oxide must typically be vented to atmosphere after passing through the system, since affordable compressors suitable for achieving the high pressures required are not reliable and readily commercially available.

In most Joule-Thomson systems, single non-ideal gasses are pressurized and then expanded through a throttling component or expansion element, to produce isenthalpic cooling. The characteristics of the gas used, such as boiling point, inversion temperature, critical temperature, and critical pressure determine the starting pressure needed to reach a desired cooling temperature. Joule-Thomson systems typically use a heat exchanger to cool the incoming high pressure gas with the outgoing expanded gas, to achieve a higher drop in temperature upon expansion and greater cooling power. For a given Joule-Thomson system, the desired cooling dictates the required heat exchanger capacity. Finned tube heat exchangers have been used, but these must be relatively long and bulky to achieve the required cooling, preventing their use in flexible cryosurgical catheters. Smaller heat exchangers have also been known, constructed of photo-etched glass plates. These heat exchange systems are still in the range of several centimeters square in size, making them still too bulky for use in flexible cryosurgical catheters. Further, these heat exchangers are planar and difficult to incorporate into tubular catheters. In these medical applications, the dimensions of the components must be less than approximately 3 mm. in width to allow incorporation into a catheter, and preferably less than 15 mm. in length to allow sufficient flexibility.

Where a small heat exchanger is placed near the distal end of a flexible catheter, the heat exchanger will necessarily be exposed to the thermal environment in that region of the patient's body. The surrounding biological tissue can impose a significant additional head load on the refrigeration system, through the heat exchanger. The heat exchanger can not normally be insulated from the thermal effects of the surrounding biological tissue, because of space limitations at that point. The additional heat load imposed on the refrigeration system by the biological tissue near the point of cooling will limit the performance of the heat exchanger, by warming both the high pressure and low pressure gas streams passing through the heat exchanger. Furthermore, the biological tissues in the vicinity of the heat exchanger can receive undesirable cooling by being exposed to the virtually uninsulated heat exchanger.

Heat exchanger requirements can be reduced somewhat by pre-cooling the gases prior to the probe tip heat exchanger. This can be done by incorporating a Peltier device in the flow path prior to the probe tip heat exchanger. Gas flowing through a heat exchanger on the surface of the cold side of the Peltier device would be cooled prior to reaching the heat exchanger near the catheter tip. Alternatively, the inlet high pressure stream could be split so that a portion of the stream could be diverted and expanded to cool the remaining portion of the inlet stream prior to reaching the heat exchanger at the catheter tip.

A dramatic improvement in cooling in refrigeration systems can be realized by using a mixture of gasses rather than a single gas. For example, the addition of hydrocarbons to nitrogen can increase the cooling power and temperature drop for a given inlet pressure. Further, it is possible to reduce the pressure and attain performance comparable to the single gas system at high pressure. Similar to single gas systems, these mixed gas systems have heat exchanger requirements and they are limited in their miniaturization potential by the size of the heat exchanger. The improvement in cooling performance realized by mixed gas systems is very desirable for flexible cryosurgical catheter systems.

Some mixed gas systems have been designed where high pressure is not a major concern, and where bulky high efficiency heat exchangers can be used, but they are typically used in defense and aerospace applications. The glass plate heat exchangers mentioned above are used in some such systems, and these systems sometimes require pressures of 1200 psia. In cryosurgical catheter applications, pressures above approximately 420 psia are undesirable for safety reasons, and because the devices exhibit poor longevity, high cost, and poor reliability. Further, a catheter which can withstand the higher pressures must typically be made of a material which is less flexible than is often desirable in a catheter. Still further, any heat exchanger which is used in a flexible cryosurgical catheter must have a width or diameter no greater than about 3 mm., and a length of no more than about 15 mm.

Specifically, it would be desirable to develop a long, slender, flexible cryosurgical catheter, for example, a transvascular cardiac catheter, which can operate at relatively low pressure while achieving the necessary cooling power to destroy biological tissue. Cardiac catheters must be very slender, in the range of less than 5 mm., and they must exhibit considerable flexibility, in order to be inserted from an access point in a remote blood vessel into the heart. A cryosurgical catheter to be used in such an application must also have a relatively low operating pressure for safety reasons. It must have the cooling capacity to overcome the ambient heat load imposed by the circulating blood, yet it must be able to achieve a sufficiently low temperature to destroy the target tissue. Finally, the cold heat transfer element must be limited to the tip or end region of the catheter, in order to prevent the damaging of tissue other than the target tissue.

It is an object of the present invention to provide a miniature refrigeration system, including a flexible cryosurgical catheter, which can achieve an expanded gas temperature of at least as low as 183 K, with sufficient cooling power to maintain this temperature when a heat load is applied, and to perform this function with an inlet high pressure of no greater than 420 psia.

BRIEF SUMMARY OF THE INVENTION

The present invention comprises a refrigeration system incorporating a flexible cryosurgical catheter with a microminiature stacked plate counterflow heat exchanger in its distal tip. The refrigeration system has a compressor for compressing a gas mixture to a pressure up to 420 psia. The high pressure gas mixture from the compressor is fed into a flexible high pressure supply tube, which can be an inner tube of a coaxial cardiac catheter. When used in this context herein, the term "high pressure" is meant to refer to the supply side of the refrigerant path, while "low pressure" refers to the return side of the refrigerant path. Both of these pressures used in the present invention are actually considerably lower than those used in prior art closed loop systems. Because of the relatively low pressure used in the present system, the catheter can be formed of a relatively pliable and flexible plastic, making the catheter suitable for microminiature cryosurgery. The supply tube of the catheter in turn feeds the high pressure gas mixture into the inlet port at the proximal end of the microminiature stacked plate counterflow heat exchanger. The high pressure gas mixture passes through a high pressure supply passageway within the stacked plate heat exchanger and exits through a port at the distal end of the heat exchanger. The high pressure distal port of the heat exchanger is connected to the inlet of an expansion element, in which the gas mixture is expanded to a lower pressure and a temperature at least as low as 183 K. The expansion element can have a second stage in which the gas mixture is further expanded isothermally to absorb additional heat from the surroundings.

The gas mixture escaping from the expansion element is exposed to the inner surface of a heat transfer element mounted in the wall of an outer tube coaxial with the inner tube. The expanded gas mixture cools the heat transfer element to a temperature of at least as low as 183 K and then returns through the low pressure return passageway of the heat exchanger. This cools the high pressure gas from its original ambient temperature to a lower temperature. From the low pressure outlet of the heat exchanger, the expanded gas mixture flows into the lumen of the outer tube, outside the inner high pressure tube, to return to the compressor.

The heat exchanger used in the present invention has a "stacked plate" laminated construction. In a preferred embodiment, the heat exchanger is constructed of a plurality of round plates and ring shaped spacers stacked alternatingly along the axial dimension of the heat exchanger. The plates have a first plurality of holes establishing the high pressure passageway of the heat exchanger, and a second plurality of holes establishing the low pressure passageway of the heat exchanger. The high pressure holes are segregated from the low pressure holes. A substantially annular channel is formed through each plate and spacer, near the periphery of the plate or spacer. This annular channel can be aligned with the annular channels through adjacent plates to establish an integral insulating vacuum jacket substantially surrounding the periphery of the heat exchanger. This integrally formed annular vacuum jacket constitutes a more uniform dead space than known vacuum jackets which are added to the outside of a heat exchanger; therefore the integral vacuum jacket achieves a more effective insulation of the heat exchanger.

The plates are formed from relatively large, very thin, oxygen free copper sheets. The copper sheet is first coated with a thin layer of a photo-resistive compound. A pattern defining the desired outline of each plate and the sizes and placement of the holes and the annular channels is designed on a computer aided design system, and the pattern is then transferred to the copper sheet with a numerically controlled laser. The laser bonds the photo-resistive layer to the copper sheet in the desired pattern. The copper sheet is then washed in etching chemicals, with the bonded pattern of photo-resistive compound protecting that portion of the copper sheet from etching. The etching chemicals dissolve the copper in the unbonded areas. This forms a large number of the desired copper plates in the sheet, with each plate having the desired pattern of holes and annular channels etched therein. This allows a large number of the copper plates to be formed from a single, large sheet. Since a large sheet can be more accurately aligned than can a very small round plate, this facilitates the accurate alignment of the copper plates with adjacent plates or spacers. This also makes the manufacturing of a large number of heat exchangers more economical.

In a similar fashion, a large number of spacer rings are formed by etching a relatively large, very thin, stainless steel sheet. Each spacer has a large opening for each high pressure passageway, and a large opening for each low pressure passageway. A substantially annular channel is formed through each spacer ring near the periphery of the spacer. This annular channel can be aligned with the annular channels through adjacent plates and spacers, to form a part of the integral insulating vacuum jacket substantially surrounding the periphery of the heat exchanger.

The large sheets of plates and spacers are stacked to form the plates and spacers into a large number of cylinders, with alternating copper plates and stainless steel spacers. Sheets of special end plates are placed at each end of the stack to form access ports at the ends of the high pressure and low pressure passageways, and to block the ends of the integral vacuum insulating jacket. The stack of copper sheets and steel sheets is then placed in a vacuum, thereby evacuating all of the high pressure and low pressure passageways, the annular channels, and the spaces between the sheets. The stack of plates and spacers is then diffusion bonded together.

When diffusion bonding is complete, the high pressure and low pressure passageways remain open through the ports at their ends, while the integral annular vacuum jacket is sealed, to maintain a vacuum. The high pressure holes in any given plate do not align perfectly with the high pressure holes in either of the neighboring plates, thereby causing the gas mixture flow to be turbulent, promoting heat transfer. The relative misalignment of holes in the copper plates, and the alignment of the holes in the spacers, can be used to achieve either a substantially axial flow, with radial heat transfer, or a substantially transverse flow, with an axial heat transfer. The annular channels in a given cylinder of plates and spacers are held in alignment, to form an axially continuous, substantially annular, vacuum jacket through virtually the entire length of the cylinder.

The stacking and diffusion bonding of relatively large sheets of plates and spacers overcomes the difficulty of trying to align individual, micro-miniature, perforated plates and spacers. Alignment of the elements is accomplished by accurate alignment of the large sheets, rather than the individual plates and spacers. The plates and spacers used in manufacturing heat exchangers for use in catheters and endoscopes must be so small that accurate alignment is virtually impossible, or very expensive. This is especially important in the heat exchanger of the present invention, where the individual holes in the high pressure passageway are slightly misaligned with the individual high pressure holes in adjacent plates, to create turbulent high pressure flow, and the low pressure holes in adjacent plates are similarly misaligned, to create turbulent low pressure flow. The turbulent flow resulting from this slight misalignment of individual holes has been found to be very important in achieving maximum heat transfer.

The stacking and diffusion bonding of relatively large sheets of plates and spacers also allows the integral formation of additional, micro-miniature, functional elements on each end of each cylinder, such as an expansion orifice on one end, and an inlet/outlet connector on the other end. A large number of expansion orifices can be etched into a large sheet and placed on the top end of the stack of sheets. Similarly, several consecutive sheets of spacer rings, without intervening copper sheets, can be placed on the bottom end of the stack of sheets, to form a connector manifold for attachment of inlet and outlet gas tubes. Without this manufacturing process, the attachment of such an expansion orifice or such an inlet/outlet connector is difficult and expensive to accomplish accurately, because of the extremely small size of such elements in a system which is suitable for use in a flexible miniature cryosurgical catheter.

The novel features of this invention, as well as the invention itself, will be best understood from the attached drawings, taken along with the following description, in which similar reference characters refer to similar parts, and in which:

BRIEF DESCRIPTION OF THE SEVERAL VIEWS OF THE DRAWINGS

FIG. 6 is an elevational view of one spacer used in the first embodiment of the micro-miniature heat exchanger used in the present invention;

FIG. 7 is an elevational view of a spacer used in a second embodiment of the microminiature heat exchanger used in the present invention;

FIG. 8 is an elevational view of a first configuration of plate used in the second embodiment of the micro-miniature heat exchanger used in the present invention;

FIG. 9 is an elevational view of a second configuration of plate used in the second embodiment of the micro-miniature heat exchanger used in the present invention, showing the different orientation of high pressure and low pressure ports;

FIG. 10 is a series of elevational views of plates and spacers used in the second embodiment of the micro-miniature heat exchanger used in the present invention, showing the flow of supply and return gas mixtures;

FIG. 11 is a sectional view of the plurality of plates and spacers shown in FIG. 10, showing the flow of supply and return gas mixtures;

FIG. 12 is a longitudinal section view of a second embodiment of the distal end portion of the cryosurgical probe used in the present invention, showing a narrow elongated heat transfer element;

FIG. 13 is a transverse section view of the second embodiment of the distal end of the probe, taken along the line 13—13 in FIG. 12;

DETAILED DESCRIPTION OF THE INVENTION

The heat exchanger of the present invention is used in a refrigeration system which uses a gas mixture, instead of a single gas, since no known single gasses are capable of achieving the necessary cooling capacity at the required temperatures, given the size limitations and pressure limitations imposed on systems intended for use in the selected applications. Several gas mixtures have been identified for use with the present invention, and it is anticipated that others will be identified as well. Appropriate gas mixtures may take various forms, and they may be either hydrocarbon-based or non-hydrocarbon-based.

Figure 1:
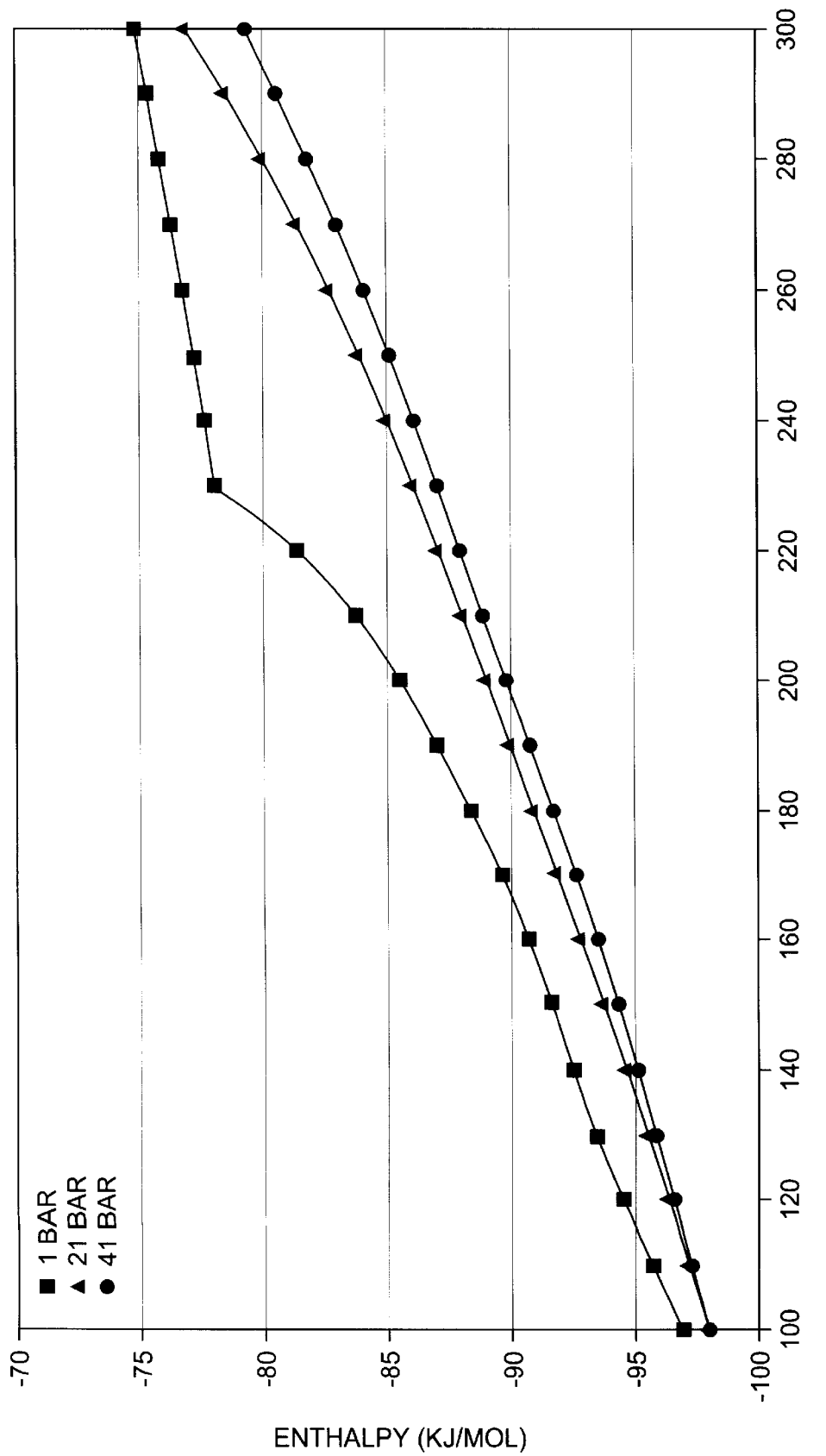
FIG. 1 is a graph of enthalpy vs. temperature for a selected gas mixture used in the cryosurgical system of the present invention.

By way of example only, the mixture currently identified as the preferred mixture for many applications is 30 percent Methane, 23 percent Nitrogen, 23 percent Isobutane, 19 percent Ethane, and 5 percent Propane. The temperature capability of isenthalpic expansion of such a gas mixture is illustrated by FIG. 1, which shows enthalpy curves for this gas mixture at pressures of 1 bar (14.5 psia.), 21 bar (305 psia), and 41 bar (595 psia). Isenthalpic expansion from one of the higher pressures to the lower pressure proceeds horizontally to the left across the graph, accompanied by a drop in temperature. The lowest temperature attainable would be at the point where the curves cross, somewhere below 100 K. The lower the temperature of the high pressure gas mixture, the lower the temperature which can be achieved by the isenthalpic expansion through the Joule-Thomson expansion element It can also be seen from the graph that there is little difference between the temperatures attainable by expanding from 41 bar and expanding from 21 bar.

For example, assume that the heat exchanger used is capable of cooling the high pressure gas mixture to a temperature of 210 K, just upstream of the expansion element. If a high pressure of 21 bar is used, the isenthalpic expansion will result in a temperature of 180 K. If the gas mixture is instead pressurized to 41 bar, the attainable temperature after isenthalpic expansion is still only about 173 K. Further, the cooling capacity, or power, represented by the difference between the high pressure curve and the I bar curve at a given temperature is similar, whether the high pressure is 21 bar or 41 bar. Therefore, the added safety achieved by lowering the initial pressure to 21 bar, or approximately 300 psia, results in only a minor loss of performance. Obviously, for a given gas mixture, the more efficient the heat exchanger, the lower the probe temperature that can ultimately be obtained, and the greater will be the cooling power.

Figure 2:
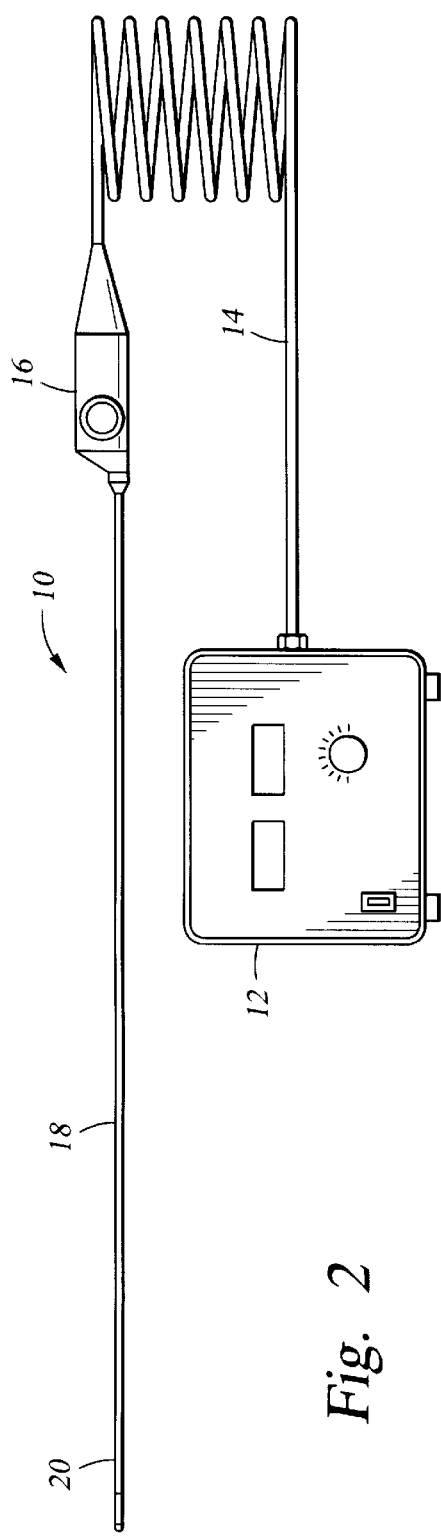
FIG. 2 is a perspective view of one embodiment of the miniature cryosurgical system of the present invention.

FIG. 2 shows a refrigeration system 10 according to the present invention, for a cryosurgical application. The system 10 consists of a commercially available single stage compressor 12, a flexible dual lumen hose 14 connected to the inlet and outlet of the compressor 12, a steering handle 16, and a cryosurgical probe 18. The compressor 12 can be any of several oil based compressors available, typically using an aftercooler, an oil separator, and an adsorption filter. Alternatively, an oil free compressor could also be utilized. The hose 14 can be any flexible dual lumen hose suitable for the pressures and chemical exposures involved, for the gas mixture used. The handle 16 can have a control expansion element installed, for the physician to use in throttling the flow rate of the gas mixture. Alternatively, the flow could be controlled via a foot switch that regulates flow at the compressor. The probe 18 is a coaxial catheter having an inner tube for conducting the high pressure gas mixture from the outlet of the compressor 12 and for returning the expanded low pressure gas to the inlet of the compressor 12. The probe 18 has a distal end portion or region 20 in which the heat exchanger, expansion element, and heat transfer element are located. The probe 18 is of suitable diameter, length, and flexibility to be inserted to the object to be cooled, such as through the vascular system of a patient into the heart. The heat exchanger is specially constructed to have a very short length, to enhance the flexibility of the distal end of the probe 18. The flexibility of the probe 18 is also enhanced by the use of relatively flexible plastic material, which is made possible by limiting the operating pressure to a relatively low level.

Figure 3:
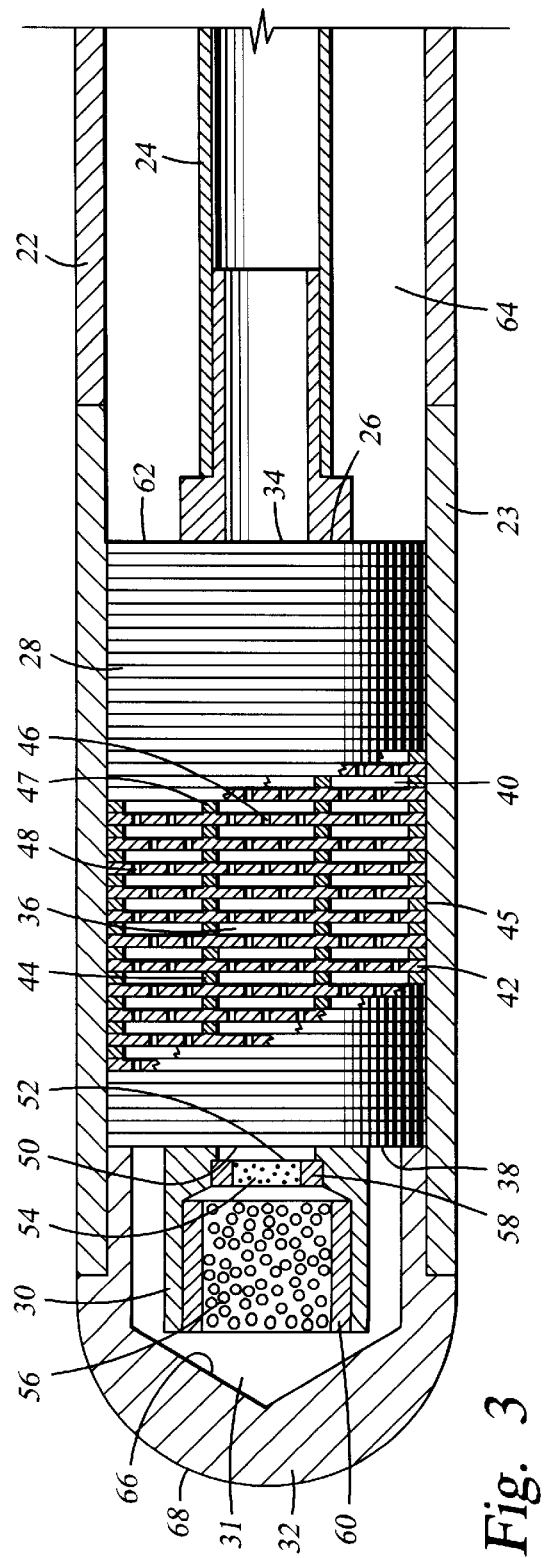
FIG. 3 is a longitudinal section view of the distal end portion of the cryosurgical probe portion of the cryosurgical system shown in FIG. 2.

FIG. 3 shows a partial section view of the distal end portion 20 of the coaxial catheter 18. The catheter 18 consists of an outer tube 22 and an inner tube 24. The outer tube 22 can be continuous to the end of the catheter 18, or it can have an extension 23, which should be considered for all practical purposes an integral part of the outer tube 22. The outer tube 22 is made according to known methods from a wire-braided polymer, such as a polyamide-ether copolymer. The inner tube 24 is made from a wire-braided polyimide having a pressure capability sufficient for the maximum high pressure anticipated for the particular application. The inner tube 24 is connected by means of an inlet fitting 26 to the proximal end of a micro-miniature heat exchanger 28. Mounted to the distal end of the heat exchanger 28 is an expansion element 30. The distal end of the expansion element 30 is exposed to a cavity 31 at the distal end of the outer tube 22 or extension 23, closed by a heat transfer element 32. The expanded gas mixture cools the inner surface 66 of the heat transfer element 32, thereby cooling the outer surface 68. The outer surface 68 is placed against the object to be cooled by the physician.

More specifically, the distal end of the inner high pressure tube 24 is connected by means of the inlet fitting 26 to the high pressure inlet port 34 at the proximal end of the heat exchanger 28. This high pressure inlet port 34 leads to a high pressure supply passageway 36 through the heat exchanger, shown as the central axial portion of the heat exchanger 28 in this embodiment. The heat exchanger 28 also has a low pressure inlet port 38 at its distal end exposed to the cavity 31. This low pressure inlet port 38 leads to a low pressure return passageway 40, shown as the outer annular portion of the heat exchanger, surrounding the high pressure passageway 36. The low pressure, low temperature gas mixture flowing through the low pressure passageway pre-cools the high pressure, higher temperature gas mixture flowing through the high pressure passageway.

The heat exchanger 28 is constructed of alternately stacked copper plates 42 and stainless steel spacers 44, diffusion bonded together. The heat exchanger 28 is shown, for the sake of simplicity in this figure, as having an outer skin over the plates 42 and spacers 44, but in actuality, the skin is optimally provided by an outer ring 45 on each spacer 44 being bonded to the extreme outer annular portion of each plate 42, as will be made more clear below. The central portion of each plate 42 has a plurality of holes 46 therethrough, which along with central openings in the spacers 44 establish the high pressure passageway 36 longitudinally through the heat exchanger 28 in the distal direction. Similarly, the outer portion of each plate 42 has a plurality of holes 48 therethrough, which along with outer openings in the spacers 44 establish the low pressure passageway 40 longitudinally through the heat exchanger 28 in the proximal direction. The high pressure passageway 36 is separated from the low pressure passageway 40 by an inner ring 47 on each spacer 44. Both the plate 42 and the spacer 44 can be provided with through channels to create an integral vacuum jacket, as will be explained below, to maximize the heat exchanger performance. This construction results in a relatively short, but relatively efficient, heat exchanger.

High pressure gas mixture passing through the heat exchanger 28 exits the high pressure passageway at a high pressure outlet port 50 at the central distal portion of the heat exchanger to enter the inlet 52 of the expansion element 30. This expansion element 30 has a first stage 54 of a first diameter, in which isenthalpic expansion to a second larger diameter takes place, lowering the temperature of the gas mixture to the design temperature. The gas mixture then passes through the second stage 56 in which isothermal expansion takes place, leaving the gas mixture still at the desired temperature, but absorbing heat from the surrounding structure in the process. The first stage 54 is constructed by filling a metal cylinder 58 with a selected size of metal beads, at a selected packing density, to achieve the desired rate of expansion of the gas. The beads are sintered in place in the cylinder 58. Similarly, the second stage 56 is constructed by filling a second metal cylinder 60 with a selected size of metal beads, at a selected packing density, to achieve the desired rate of expansion of the gas. Typically, the beads in the second stage 56 will have a larger surface area to enhance heat transfer. Alternatively, rather than a sintered bead expansion element, an expansion orifice could be used as the expansion element. Reference to the sintered bead expansion element hereinafter is understood to include reference to an expansion orifice.

The expanded gas mixture which passes through the heat exchanger 28 in the proximal direction exits the annular low pressure passageway 40 at a low pressure outlet port 62 at the proximal end of the heat exchanger 28. This expanded gas mixture enters the inner lumen 64 of the outer tube 22, surrounding the inner tube 24, to be returned to the compressor 12.

Figure 5:
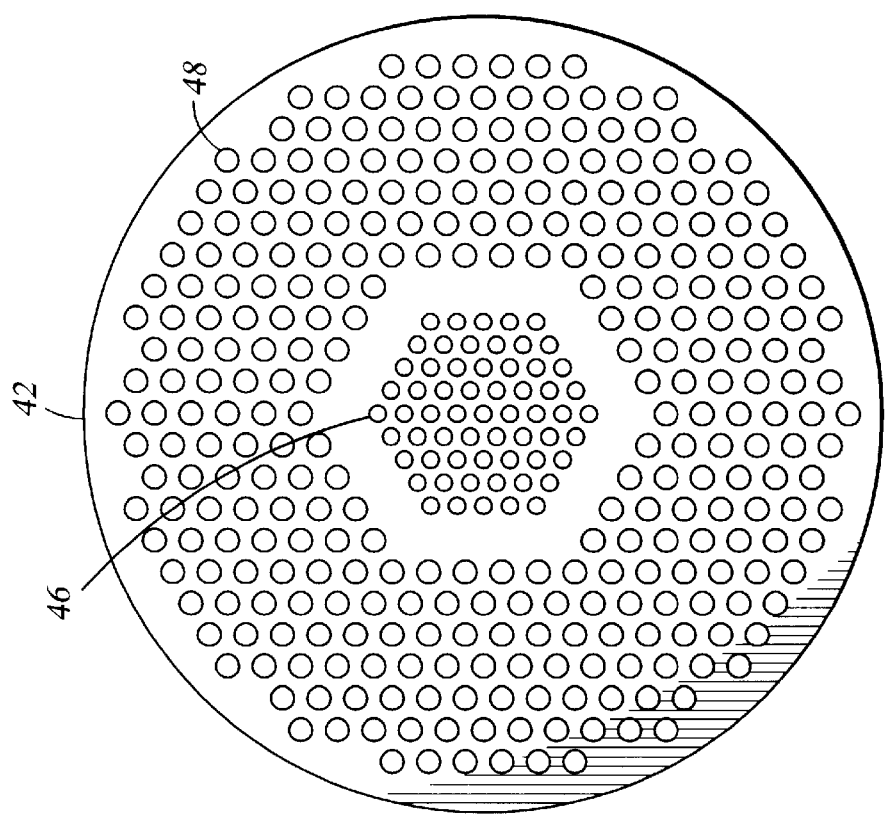
FIG. 5 is an elevational view of a second configuration of heat exchanger plate for use in the first embodiment of the heat exchanger, showing a different angular orientation of holes from the orientation shown in FIG. 4.
Figure 4:
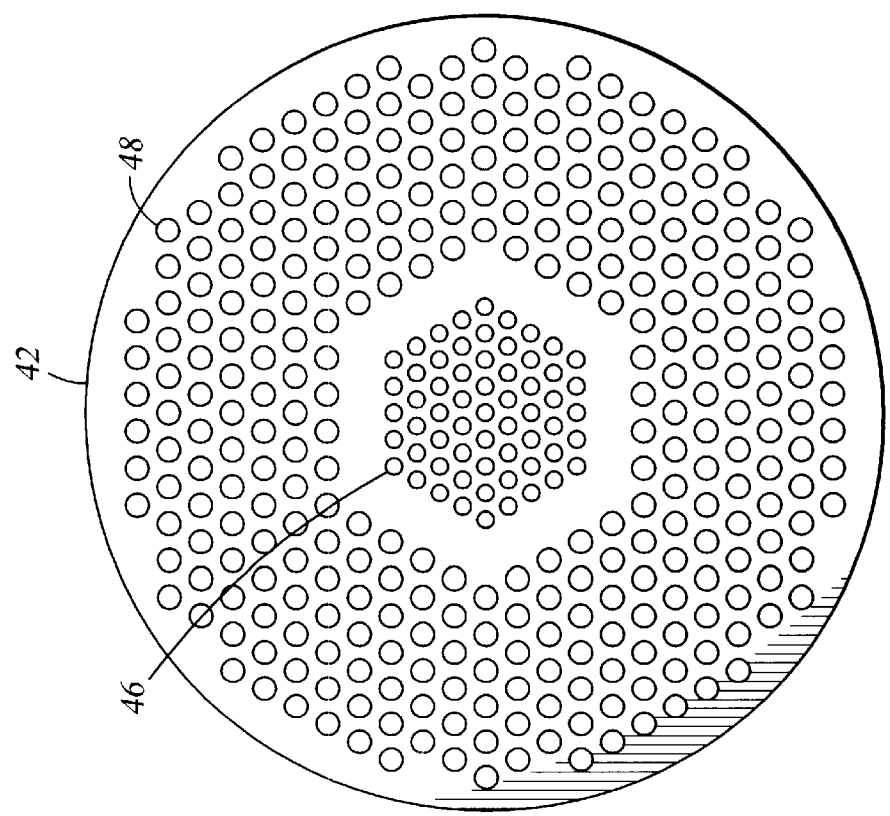
FIG. 4 is an elevational view of a first configuration of heat exchanger plate used in a first embodiment of the micro-miniature heat exchanger used in the present invention.

FIGS. 4 and 5 more clearly illustrate the structure of the plates 42 and their angular orientation within one embodiment of the heat exchanger 28. Each plate 42 has a first plurality of high pressure holes 46 through its central portion, and a second plurality of low pressure holes 48 through its outer annular portion. Typically, the diameter and spacing of the inner holes 46 are smaller than the diameter and spacing of the outer holes 48. Selection of hole diameter and spacing for the two different passageways is designed for an optimization of minimum pressure drop and maximum heat transfer rate at the two different pressures, according to well known design principles.

FIGS. 4 and 5 are also intended to show the relative angular orientation between adjacent plates 42. It can be seen that the two figures actually depict the same plate configuration, with the plate 42 in FIG. 5 simply being rotated relative to the plate 42 in FIG. 4. The hole pattern used in the plate 42 can be varied, with the objective being to maximize the heat exchange contact between the gas mixture and the plate 42. Gas does not flow from the high pressure portion of the plate to the low pressure portion, being prevented by contact between the plate 42 and the inner ring 47 of the interdisposed spacer 44, as shown earlier in FIG. 3. The relative angular orientation between adjacent plates 42 can also be varied according to the chosen hole pattern, with the objective being to maximize turbulence of the gas mixture, to promote heat transfer. Maximizing heat transfer results in the shortest, smallest diameter, heat exchanger possible, which in turn results in a more flexible probe tip.

It can be clearly seen from FIGS. 3, 4, and 5 that gas flowing through the heat exchanger 28 in either of the passageways 36, 40 follows a somewhat tortuous path, with a substantial portion of the flow path being involved in movement transverse to the axis of the heat exchanger 28. In the embodiment shown, the transverse component of the flow results from the relative angular orientation between adjacent plates 42. This tortuous path promotes efficient heat transfer, allowing the micro-miniature heat exchanger 28 to achieve the required temperature drop to enable the desired expansion through the expansion element 30, ultimately producing the designed cooling temperature. Heat flow in this embodiment tends to be substantially radial.

FIG. 6 shows one embodiment of the spacer 44, which is interspersed between the plates 42. The spacer 44 has an outer ring 45 and an inner ring 47 supported in the desired concentric relationship by spokes 70. An inner opening 72 within the inner ring 47 serves as a portion of the high pressure passageway 36 between plates 42. A plurality of outer openings 74 between the inner ring 47 and the outer ring 45 serve as a portion of the low pressure passageway 40 between plates 42. The inner ring 47 serves as a divider between the high and low pressure openings 72, 74.

FIG. 7 shows a second embodiment of the spacer 44' which can be used with a second embodiment of plates 42' shown in FIGS. 8 and 9. The spacer 44' has an outer ring 45' and a high/low pressure divider 47'. This divider 47' separates the high pressure opening 72' from the low pressure opening 74'. It can be seen that this spacer 44' can be turned over from the orientation shown in FIG. 7, to reverse the orientation of the divider 47', for reasons that will become apparent below. FIG. 8 shows a plate 42' having a relatively small rectangular high pressure hole 46' and a relatively large rectangular low pressure hole 48', with the long dimensions of the rectangular holes 46', 48' being vertically aligned. FIG. 9 shows the same type of plate 42', with the rectangular holes 46', 48' being arranged horizontally. These two hole patterns and the two spacer orientation possible with the spacer 44' are used to create a series of adjacent plates 42' and spacers 44' as shown in FIG. 10.

FIG. 10 shows this series arranged from left to right as they would be arranged from the proximal end of the heat exchanger toward the low pressure end, in successive series. The HP arrows show the flow path of the high pressure gas mixture into the plane of the page, while the LP arrows show the path of the low pressure gas mixture out of the plane of the page. FIG. 11 further illustrates this flow path, by showing a vertical section through the stacked plates 42' and spacers 44'. Dashed lines are used to show the locations of hidden high and low pressure holes. Here again, it can be seen that the gas mixture follows a tortuous path through both the high pressure and low pressure passageways 36, 40, but in this embodiment, the transverse components of the flow are much more pronounced than in the first embodiment, and the heat flow tends to be more axial than radial.

FIGS. 12 and 13 show a second embodiment of the distal end portion of the catheter 18', having a slender elongated heat transfer element 32'. This embodiment illustrates that the end portion of the catheter can have a fluid tube 27 affixed to the expansion element 30, a fluid chamber 29, and insulation 25 between the fluid chamber 29 and the extension tube 23. This construction insures that the cooling power is applied primarily through the heat transfer element 32'.

Figure 15:
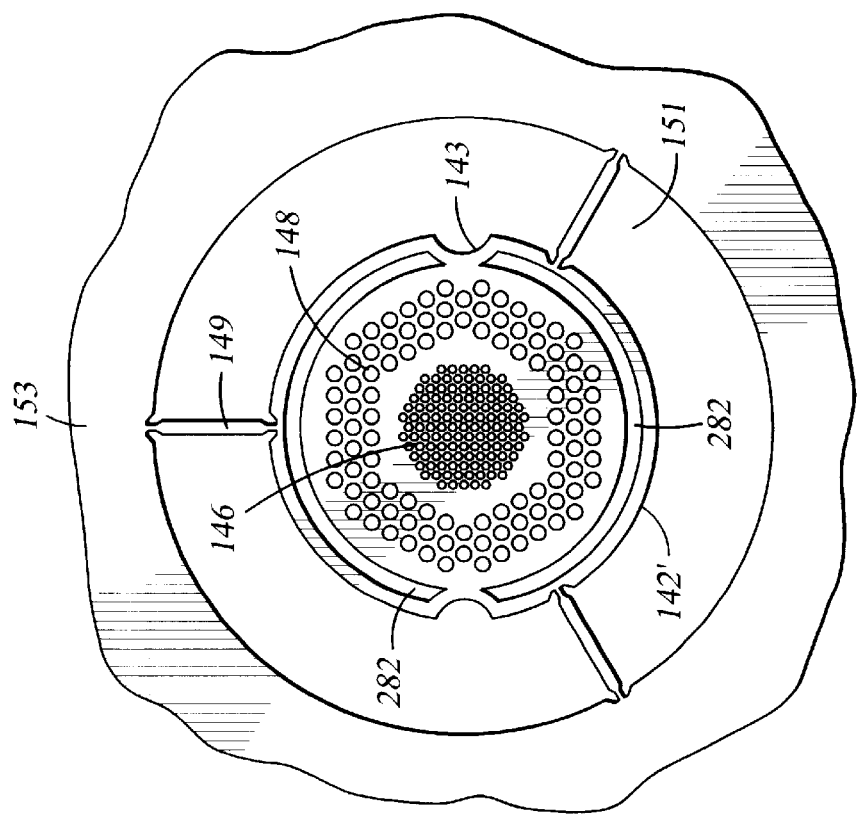
FIGS. 14 and 15 are elevational views of two configurations of heat exchanger plates used in a third embodiment of the heat exchanger used in the present invention.
Figure 14:
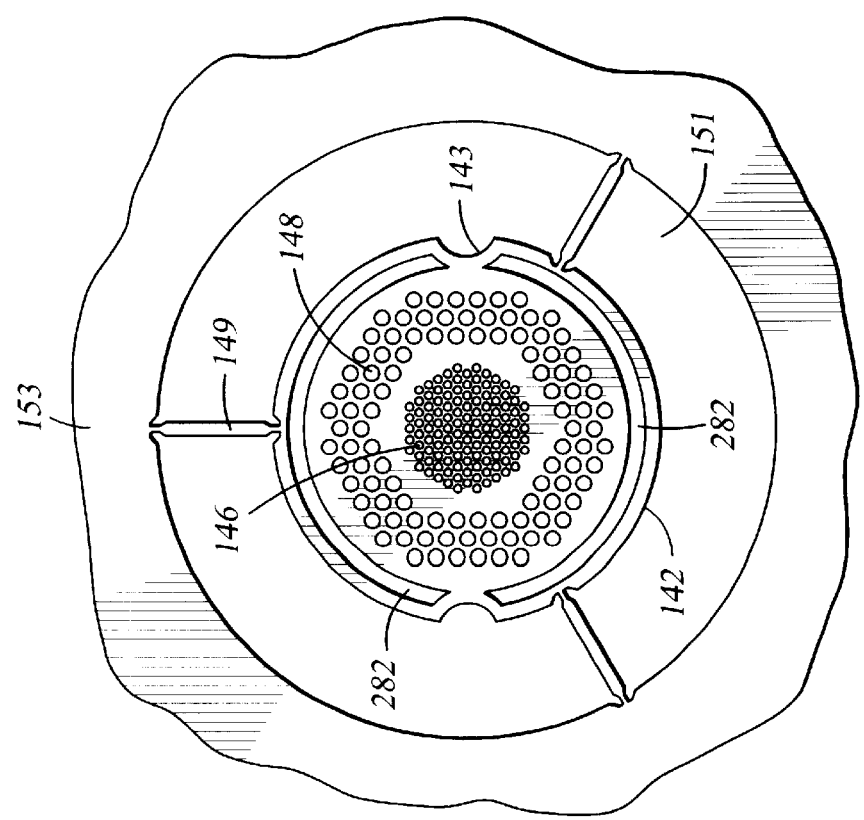

FIGS. 14 and 15 show heat exchanger plates 142, 142' which can be used in a third embodiment of the heat exchanger used in the present invention. They are formed from a sheet 153 of material, such as a metal, which has a relatively high coefficient of heat transfer. As an example, the sheet 153 from which the plates 142, 142' are made can be an oxygen free copper sheet. As will be explained, the heat exchanger will be constructed by laminating alternating plates 142 and 142', separated by spacers. Each plate 142, 142' includes a plurality of indentations or cutouts 143, to form side grooves in the final assembly. This allows instrumentation wires to be carried to the tip of the catheter, were they can monitor temperature or electrical conduction of the heart.

Each plate 142, 142' includes a centrally located pattern of high pressure holes 146, which form a high pressure gas passageway, and an annular pattern of low pressure holes 148, which form a low pressure gas passageway. Each plate 142, 142' also has a substantially annular channel 282 formed therethrough, to form a vacuum jacket as will be explained below. As shown, the annular channel 282 may be formed as two or more substantially annular channel segments to clear the cutouts 143. When first formed from the sheet 153, the plate 142, 142' is supported from the sheet 153 by a plurality of elongate struts 149. A plurality of open voids 151 surround each plate 142, 142', between the plate 142, 142' and the remainder of the sheet 153. It can be seen that the central pattern of high pressure holes 146 in plate 142' is oriented at a 30° angle relative to the central pattern of high pressure holes 146 in plate 142. This insures that each high pressure hole 146 in plate 142 is not substantially aligned with a high pressure hole 146 in the adjacent plate 142'. Similarly, the annular pattern of low pressure holes 148 in plate 142' is oriented at a 30° angle relative to the annular pattern of low pressure holes 148 in plate 142. This relative angular orientation can vary, but it must be sufficient to cause turbulent flow, rather than laminar flow, as gas flows from plate 142 to the adjacent plate 142', or vice versa This turbulent gas flow promotes heat transfer from the high pressure gas to the plate 142, 142' in the central region, and it promotes heat transfer from the plate 142, 142' to the low pressure gas in the annular region around the central region. This is also important because the fluid mixtures used in the system are sometimes part liquid, and better heat transfer occurs as the liquid splashes on the copper surface, rather than passing straight through the holes.

Figure 16:
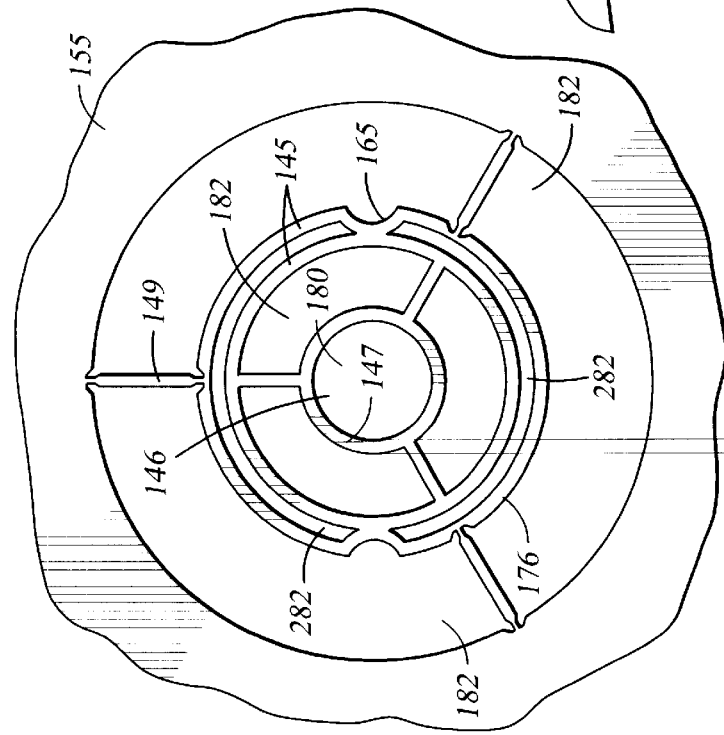
FIG. 16 is an elevational view of a spacer used in the third embodiment of the heat exchanger used in the present invention, with the plates shown in FIGS. 14 and 15.

FIG. 16 shows a spacer 176 suitable for use with the plate 142, 142' shown in FIGS. 14 and 15. The outer periphery of the spacer 176 is formed by a double outer ring 145, with the two limbs of the outer ring 145 being separated by a substantially annular channel 282. In addition to the outer ring 145, the spacer 176 is partitioned by a ring-shaped partition 147. The ring partition 147 encloses a high pressure chamber 180 designed to encompass the high pressure holes 146 in adjacent plates 142, 142'. Between the ring partition 147 and the outer ring 145 are a plurality of low pressure chambers 182. The low pressure chambers 182 are designed to generally encompass the low pressure holes 148 in the adjacent plates 142, 142'. The ring partition 147 has a width 184 sufficient to seal the high pressure chamber 180 from the low pressure chambers 182. It can be seen that, after assembly and lamination of the heat exchanger, with spacers 176 between adjacent plates 142, 142', the ring partitions 147 isolate the high pressure chambers 180 from the low pressure chambers 182, to create a high pressure passageway and a low pressure passageway through the heat exchanger. The high pressure passageway is substantially along the longitudinal axis of the heat exchanger, while the low pressure passageway is substantially coaxial with the high pressure passageway. Therefore, both high pressure and low pressure gas flows substantially axially through the heat exchanger, and heat transfer is substantially transverse to the axis, in this case being outwardly radial from the high pressure passageway to the low pressure passageway. Other arrangements of the passageways could be used which would result in transverse heat flow that would not be radial, without departing from the spirit of the invention. It also can be seen that, after assembly and lamination of the heat exchanger, with spacers 176 between adjacent plates 142, 142', the annular channels 282 in the plates and spacers align to create an integral, substantially annular, vacuum jacket around the periphery of the heat exchanger. The vacuum jacket is substantially coaxial with the longitudinal axis of the heat exchanger. Since, in this configuration, the high pressure passageway is along the axis, and the low pressure passageway is coaxial with the high pressure passageway, in an annular region, the spacer 176 can also function as a manifold to connect the high pressure gas flow to a central inlet port or outlet orifice, at the ends of the heat exchanger, and to connect the low pressure gas flow to an annular inlet or outlet port, as will be discussed below.

Every spacer or manifold used in the heat exchanger will have a common or standard outer profile. The outer profile is supported and separated from the sheet 155 from which the spacers and manifolds are made by a plurality of struts 149. The spacers and manifolds are formed from a sheet 155 of material, such as a metal, which can have a relatively lower coefficient of heat transfer than the material from which the plates 142, 142' are made. As an example, the sheet 155 from which the spacers and manifolds are made can be stainless steel. The use of a relatively harder material for the spacers and manifolds promotes the durability of the heat exchanger. The outer diameter of the standard outer profile of the spacers 176 matches the outer diameter of the plates 142, 142'. The standard outer profile has a plurality of indentations 165 which align with the indentations 143 of the plates 142, 142'. The centers of curvature of the indentations 165 align with the corresponding centers of curvature of the indentations 143 in the plates 142, 142', to insure alignment of all the plates, spacers, and manifolds when the heat exchanger is assembled.

Figure 17:
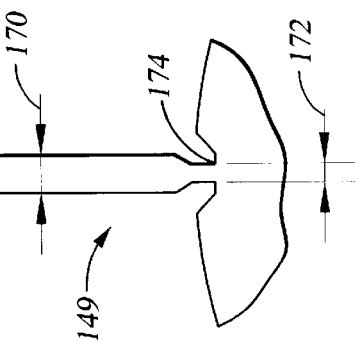
FIG. 17 is an elevational view of a strut used to connect the plates and spacers to their respective sheets, during construction of the heat exchanger used in the present invention.

As shown in FIG. 17, the strut 149 used to support and locate the plate 142, 142' within the copper sheet 153, and to support and locate the spacer or manifold within the stainless steel sheet 155 has a major width 170 which is sufficient to provide the necessary support and positioning. In addition, the strut 149 has a reduced width 172 at each end, to facilitate breaking of the plate, spacer, or manifold from its sheet, after lamination of the sheets has been accomplished. Further, a sharp corner 174 is provided where the strut 149 joins the sheet 153, 155, to increase the ease of removal of the strut 149 from the sheet and the plate, spacer, or manifold.

Figure 18:
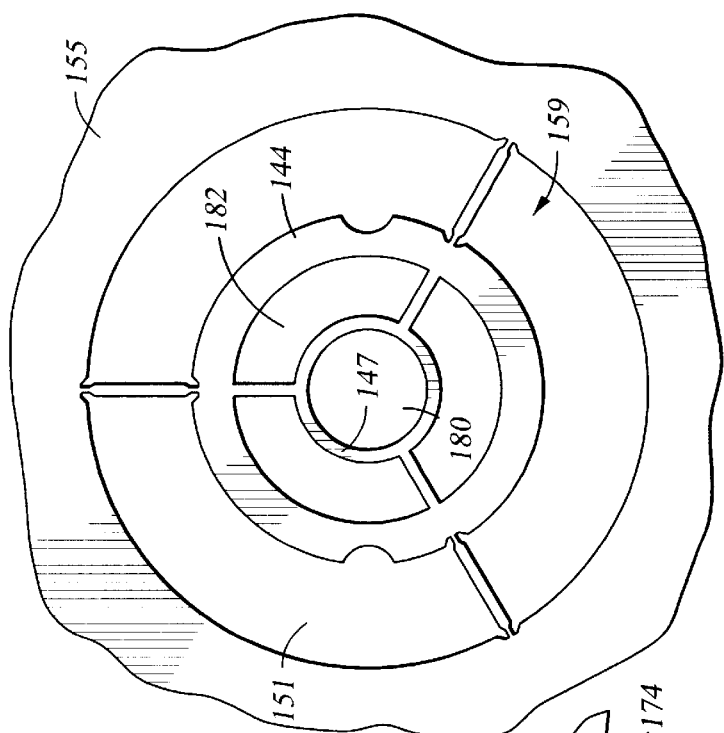
FIG. 18 is an elevational view of an end cap used with the plates shown in FIGS. 14 and 15 and the spacer shown in FIG. 16.

FIG. 18 shows an end cap 159 suitable for use with the plates 142, 142' shown in FIGS. 14 and 15, and with the spacer 176 shown in FIG. 16. The outer periphery of the end cap 159 is formed by a single outer ring 144. The single outer ring 144 has a width equal to the overall width of the double outer ring 145 of the spacer 176. In addition to the single outer ring 144, which exhibits the standard outer profile discussed above, the end cap 159 is partitioned by a ring-shaped partition 147 identical to the ring shaped partition 147 of the spacer 176. The ring partition 147 encloses a high pressure chamber 180. Between the ring partition 147 and the outer ring 144 are a plurality of low pressure chambers 182. It can be seen that, after assembly and lamination of the heat exchanger, with spacers 176 between adjacent plates 142, 142', and with an end cap 159 on each end, the vacuum jacket formed integrally in the wall of the heat exchanger by the alignment of the annular channels 282 is capped at each end.

Figure 20:
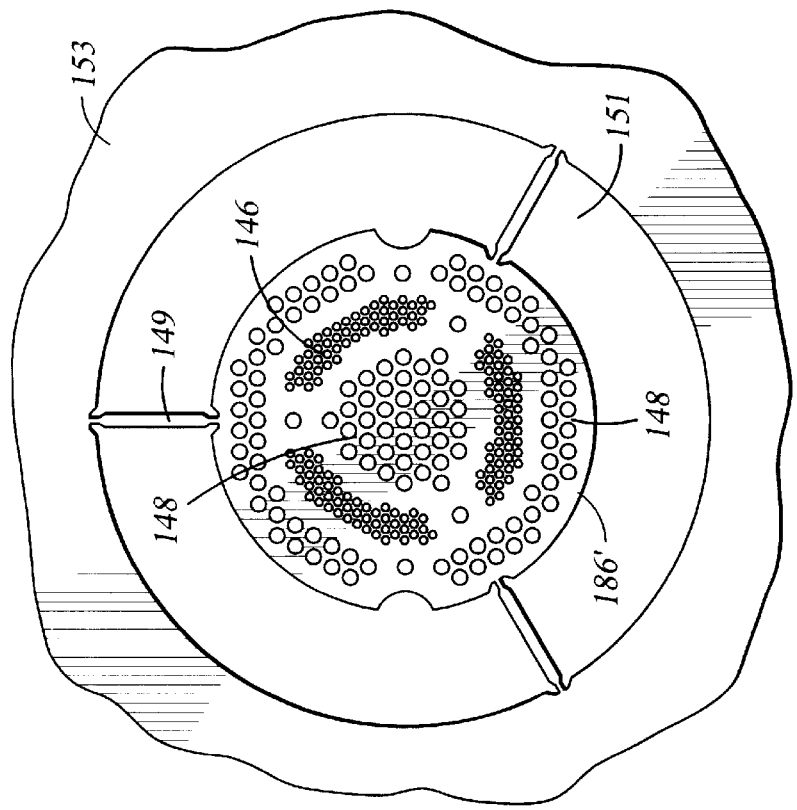
FIGS. 19 and 20 are elevational views of a heat exchanger plate used in a fourth embodiment of the heat exchanger used in the present invention.
Figure 19:
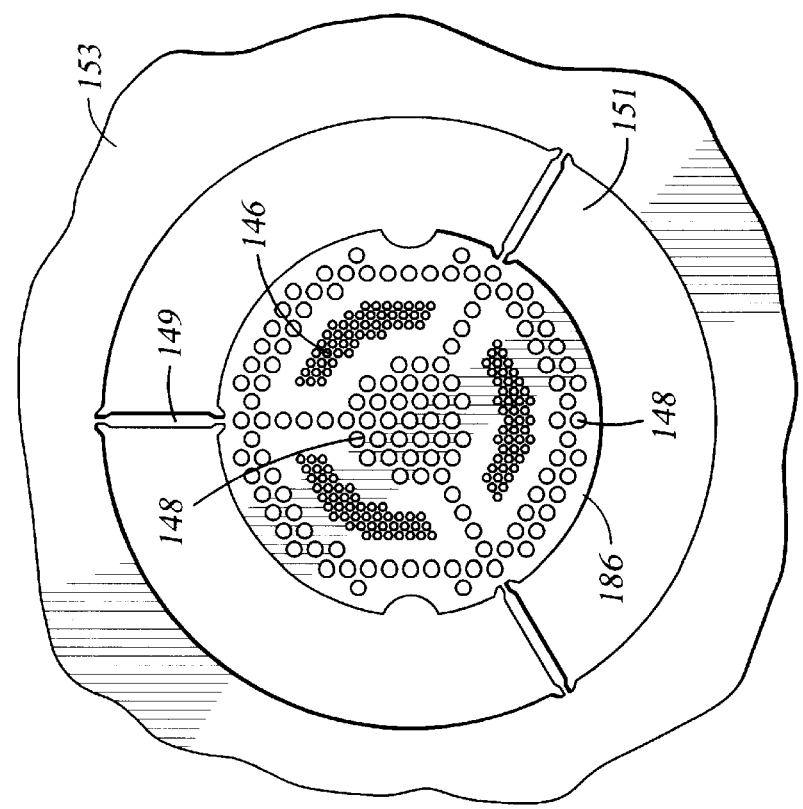

FIGS. 19 and 20 show a fourth configuration of heat exchanger plates 186, 186' which can result in more efficient heat transfer than the third configuration shown in FIGS. 14 and 15. Each plate 186, 186' includes a centrally located pattern of low pressure holes 148, along with an annular pattern of low pressure holes 148, to form a coaxial low pressure gas passageway. Each plate 186, 186' also includes an annular pattern of high pressure holes 146, to form a high pressure gas passageway. These high pressure holes are arranged in three groups, coaxial with and sandwiched between the central pattern and the annular pattern of low pressure holes 148. The high pressure passageway in this configuration is substantially coaxial with the longitudinal axis of the heat exchanger, while the low pressure passageway has a central region along the axis, and an outer annular region which is substantially coaxial with the high pressure passageway. Therefore, both high pressure and low pressure gas flows substantially axially through the heat exchanger, and heat transfer is substantially transverse to the axis, in this case being both inwardly and outwardly radial from the high pressure passageway to the two regions of the low pressure passageway. When first formed from the sheet 153, the plate 186, 186' is supported from the sheet 153 by a plurality of elongate struts 149. A plurality of open voids 151 surround each plate 186, 186', between the plate 186, 186' and the remainder of the sheet 153.

It can be seen that the three groups of high pressure holes 146 in plate 186' generally align with the three groups of high pressure holes 146 in plate 186. . However, each of the three groups on plate 186' is shaped differently from its corresponding group on adjacent plate 186, to cause a substantial misalignment of the individual holes, promoting turbulent high pressure gas flow. Similarly, the central pattern of low pressure holes 148 in plate 186' generally aligns with the central pattern of low pressure holes 148 in plate 186. However, the central pattern on plate 186' is shaped differently from the central pattern on adjacent plate 186, to cause a substantial misalignment of the individual holes, promoting turbulent low pressure flow. On the other hand, the outer annular pattern of low pressure holes 148 in plate 186' is oriented at a 30° angle relative to the outer annular pattern of low pressure holes 148 in plate 186. This insures that each low pressure hole 148 in the outer annular pattern in plate 186 is not substantially aligned with a low pressure hole 148 in the adjacent plate 186'. This relative angular orientation of the outer annular patterns can vary, but it must be sufficient to cause turbulent flow, rather than laminar flow, as low pressure gas flows from plate 186 to the adjacent plate 186', or vice versa. This turbulent high pressure gas flow promotes heat transfer from the high pressure gas to the plate 186, 186' in the sandwiched annular region, and the turbulent low pressure gas flow promotes heat transfer from the plate 186, 186' to the low pressure gas in the central region and in the outer annular region.

While annular channels 282 are not shown in the plates of FIGS. 19 and 20, as they are in the plates of FIGS. 14 and 15, it should be understood that these and all other embodiments of the plates disclosed herein could incorporate annular channels 282 as well, to form a heat exchanger having an integral vacuum jacket. Where the annular channels 282 are incorporated in the plates and spacers, an end cap similar to the end cap 159 shown in FIG. 18 having a single, wide, outer ring would be used on each end of the heat exchanger, to enclose the integral vacuum jacket.

Figure 21:
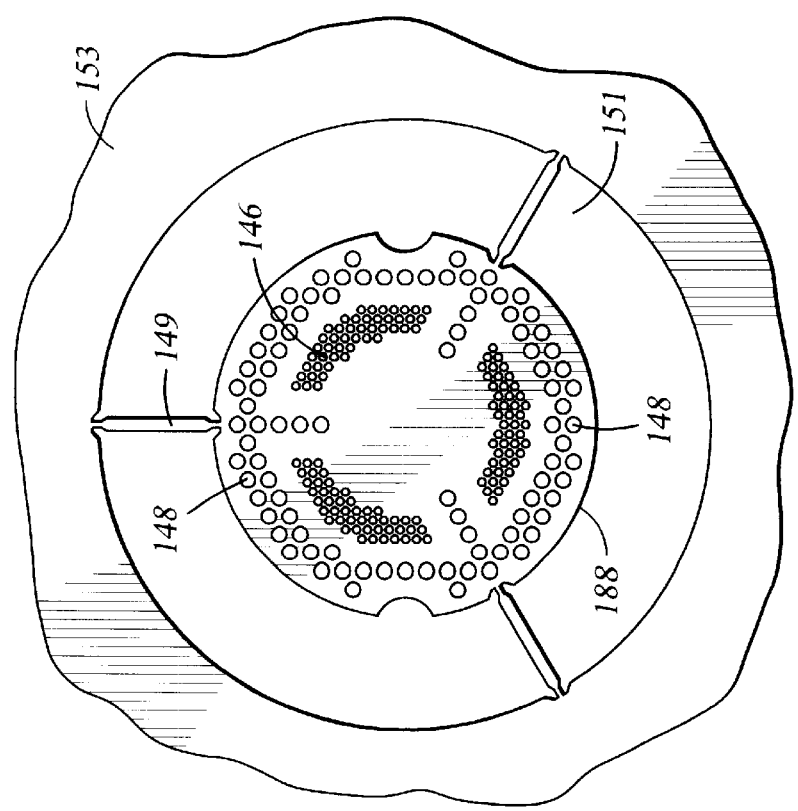
FIG. 21 is an elevational view of an end plate used with the plates shown in FIGS. 19 and 20.

As differentiated from the configuration of plates shown in FIGS. 14 and 15, the configuration shown in FIGS. 19 and 20 requires a special end plate to facilitate connection to the two ends of the heat exchanger. FIG. 21 shows such an end plate 188. In the end plate 188, the central pattern of low pressure holes has been eliminated, while the annular pattern of high pressure holes 146 and the outer annular pattern of low pressure holes 148 remain essentially the same as seen in plate 186, shown in FIG. 19. Elimination of the central pattern of low pressure holes from the end plate 188 facilitates the manifolding of the high pressure gas flow to a central inlet port or outlet orifice, and the manifolding of the low pressure gas flow to an annular inlet or outlet port, as will be discussed below.

Figure 22:
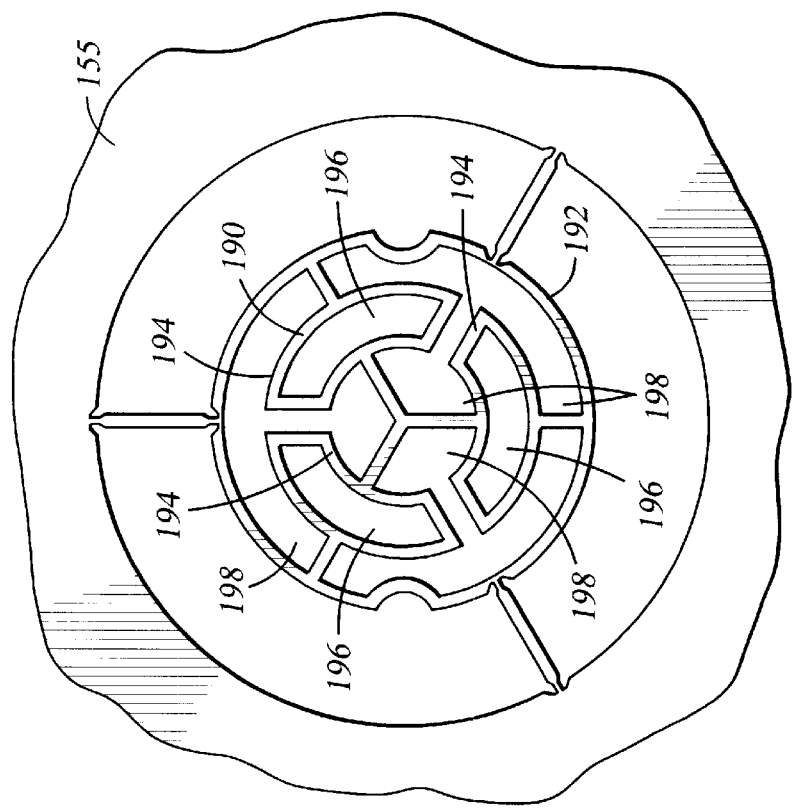
FIG. 22 is an elevational view of a spacer used with the plates shown in FIGS. 19 and 20.

FIG. 22 shows a spacer 190 suitable for use with the plate 186, 186' shown in FIGS. 19 and 20. In addition to an outer ring 192, which exhibits the standard outer profile discussed above, the spacer 190 is partitioned by three annular partitions 194. The annular partitions 194 enclose three high pressure chambers 196 designed to encompass the high pressure holes 146 arranged in three annular groups in adjacent plates 186, 186'. Between the annular partitions 194 and the outer ring 192 are a plurality of low pressure chambers 198. The low pressure chambers 198 are designed to generally encompass the low pressure holes 148 arranged in a central pattern and an outer annular pattern in the adjacent plates 186, 186'. The annular partitions 194 have a width sufficient to seal the high pressure chambers 196 from the low pressure chambers 198. It can be seen that, after assembly and lamination of the heat exchanger, with spacers 190 between adjacent plates 186, 186', the annular partitions 194 isolate the high pressure chambers 196 from the low pressure chambers 198, to create a high pressure passageway and a low pressure passageway through the heat exchanger. As mentioned above, the high pressure passageway in this configuration is substantially coaxial with the longitudinal axis of the heat exchanger, while the low pressure passageway has a central region along the axis, and an outer annular region which is outside, and substantially coaxial with, the high pressure passageway. Therefore, both high pressure and low pressure gas flows substantially axially through the heat exchanger, and heat transfer is substantially transverse to the axis, in this case being both inwardly and outwardly radial from the high pressure passageway to the two regions of the low pressure passageway.

While annular channels 282 are not shown in the spacer of FIG. 22, as they are in the spacer of FIG. 16, it should be understood that this and all other embodiments of the spacers disclosed herein could incorporate annular channels 282 as well, to form a heat exchanger having an integral vacuum jacket. Where the annular channels 282 are incorporated in the plates and spacers, an end cap similar to the end cap 159 shown in FIG. 20 having a single, wide, outer ring would be used on each end of the heat exchanger, to enclose the integral vacuum jacket.

Figure 23:
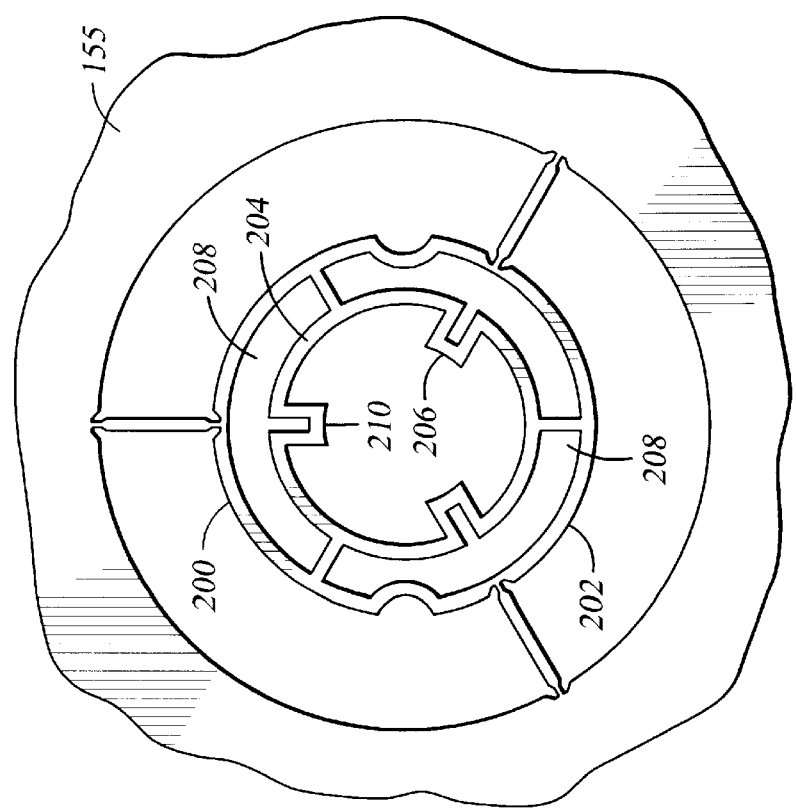
FIG. 23 is an elevational view of an end manifold used with the plates shown in FIGS. 19 and 20.

FIG. 23 shows a manifold 200 suitable for use with the plate 186, 186' shown in FIGS. 19 and 20, and with the end plate shown in FIG. 21. In addition to an outer ring 202, which exhibits the standard outer profile, the manifold 200 is partitioned by an irregular ring-shaped partition 204. The ring partition 204 encloses a high pressure chamber 206 designed to encompass the high pressure holes 146, in end plates 188. By virtue of indentations 210, the ring partition 204 also excludes the low pressure holes 148 in end plates 188. Between the ring partition 204 and the outer ring 202 are a plurality of low pressure chambers 208. The low pressure chambers 208 are designed to generally encompass the low pressure holes 148 in the end plates 188. The ring partition 204 has a width sufficient to seal the high pressure chamber 206 from the low pressure chambers 208. It can be seen that, after assembly and lamination of the heat exchanger, with spacers 190 between adjacent plates 186, 186', with end plates 188 on each end, and with manifolds 200 outside the end plates 188, the ring partitions 204 manifold the high pressure passageway to a central location and manifold the low pressure passageway to an outer annular location. This allows connection of the high pressure gas flow to a central inlet port or outlet orifice, at the ends of the heat exchanger, and to connect the low pressure gas flow to an annular inlet or outlet port, as will be discussed below.

Figure 24:
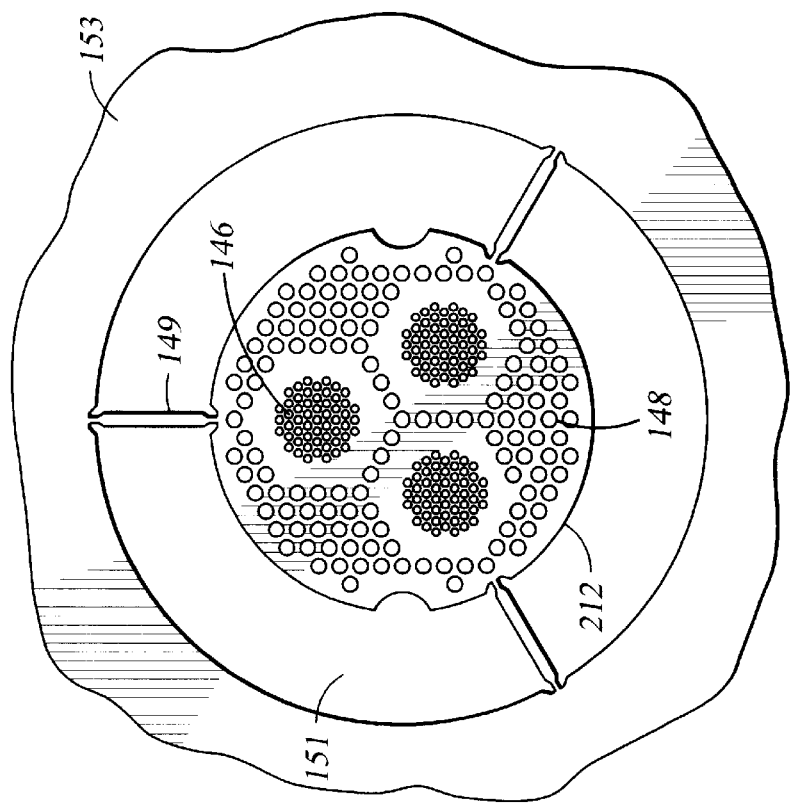
FIGS. 24 and 25 are elevational views of a heat exchanger plate used in a fifth embodiment of the heat exchanger used in the present invention.
Figure 25:
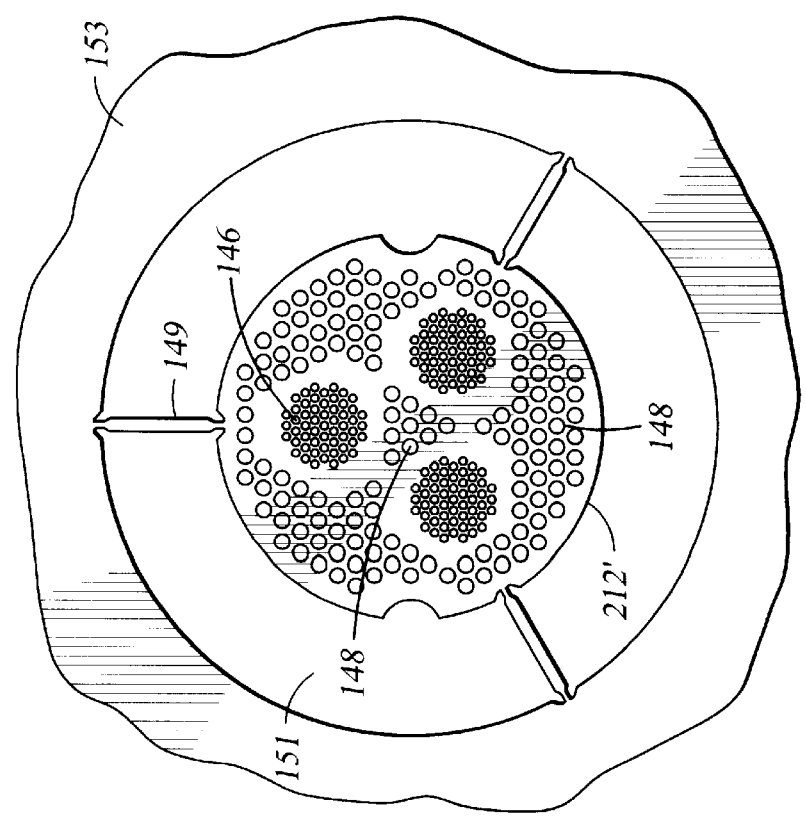

FIGS. 24 and 25 show a fifth configuration of heat exchanger plates 212, 212'. Each plate 212, 212' includes a centrally located pattern of low pressure holes 148, along with an annular pattern of low pressure holes 148, to form a coaxial low pressure gas passageway. Each plate 212, 212' also includes a pattern of high pressure holes 146, to form a high pressure gas passageway. These high pressure holes 146 are arranged in three round groups, coaxial with and sandwiched between the central pattern and the annular pattern of low pressure holes 148. The high pressure passageway in this configuration is in three regions that are substantially parallel with the longitudinal axis of the heat exchanger, while the low pressure passageway has a central region along the axis, and an outer annular region which is substantially coaxial with the high pressure passageway. Therefore, both high pressure and low pressure gas flows substantially axially through the heat exchanger, and heat transfer is substantially transverse to the axis, in this case being both inwardly and outwardly radial from the three regions of the high pressure passageway to the two regions of the low pressure passageway. When first formed from the sheet 153, the plate 212, 212' is supported from the sheet 153 by a plurality of elongate struts 149. A plurality of open voids 151 surround each plate 212, 212', between the plate 212, 212' and the remainder of the sheet 153.

It can be seen that the three groups of high pressure holes 146 in plate 212' generally align with the three groups of high pressure holes 146 in plate 212. However, each of the three groups on plate 212' is oriented at a 30° angle relative to its corresponding group of high pressure holes 146 in plate 212. This insures that each high pressure hole 146 in the three groups in plate 212 is not substantially aligned with a high pressure hole 146 in the adjacent plate 212'. This relative angular orientation of each of the three groups can vary, but it must be sufficient to cause turbulent flow, rather than laminar flow, as high pressure gas flows from plate 212 to the adjacent plate 212', or vice versa. Similarly, the outer annular pattern of low pressure holes 148 in plate 212' is oriented at a 30° angle relative to the outer annular pattern of low pressure holes 148 in plate 212. This insures that each low pressure hole 148 in the outer annular pattern in plate 212 is not substantially aligned with a low pressure hole 148 in the adjacent plate 212'. This relative angular orientation of the outer annular patterns can vary, but it must be sufficient to cause turbulent flow, rather than laminar flow, as low pressure gas flows from plate 212 to the adjacent plate 212', or vice versa. On the other hand, the central pattern of low pressure holes 148 in plate 212' generally aligns with the central pattern of low pressure holes 148 in plate 212. However, the central pattern on plate 212' is shaped differently from the central pattern on adjacent plate 212, to cause a substantial misalignment of the individual holes, promoting turbulent low pressure flow. This turbulent high pressure gas flow promotes heat transfer from the high pressure gas to the plate 212, 212' around the three high pressure groups, and the turbulent low pressure gas flow promotes heat transfer from the plate 212, 212' to the low pressure gas in the central region and in the outer annular region.

Figure 26:
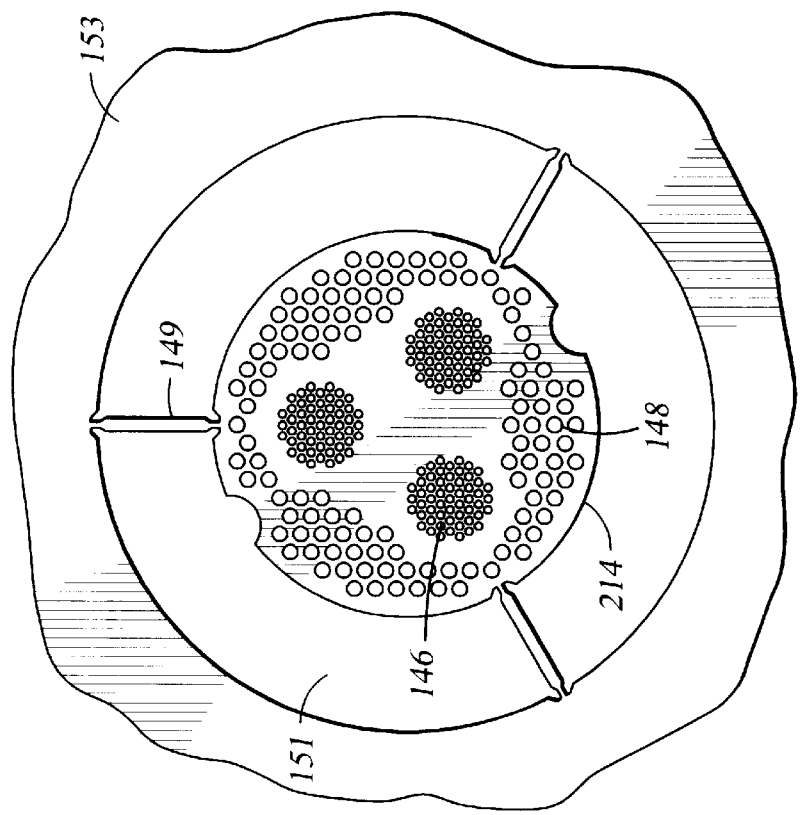
FIG. 26 is an elevational view of an end plate used with the plates shown in FIGS. 24 and 25.

Similarly to the configuration of plates shown in FIGS. 19 and 20, the configuration shown in FIGS. 24 and 25 requires a special end plate to facilitate connection to the two ends of the heat exchanger. FIG. 26 shows such an end plate 214. In the end plate 214, the central pattern of low pressure holes has been eliminated, while the pattern of high pressure holes 146 and the outer annular pattern of low pressure holes 148 remain essentially the same as seen in plate 212, shown in FIG. 24. Elimination of the central pattern of low pressure holes from the end plate 214 facilitates the manifolding of the high pressure gas flow to a central inlet port or outlet orifice, and the manifolding of the low pressure gas flow to an annular inlet or outlet port, as will be discussed below.

Figure 27:
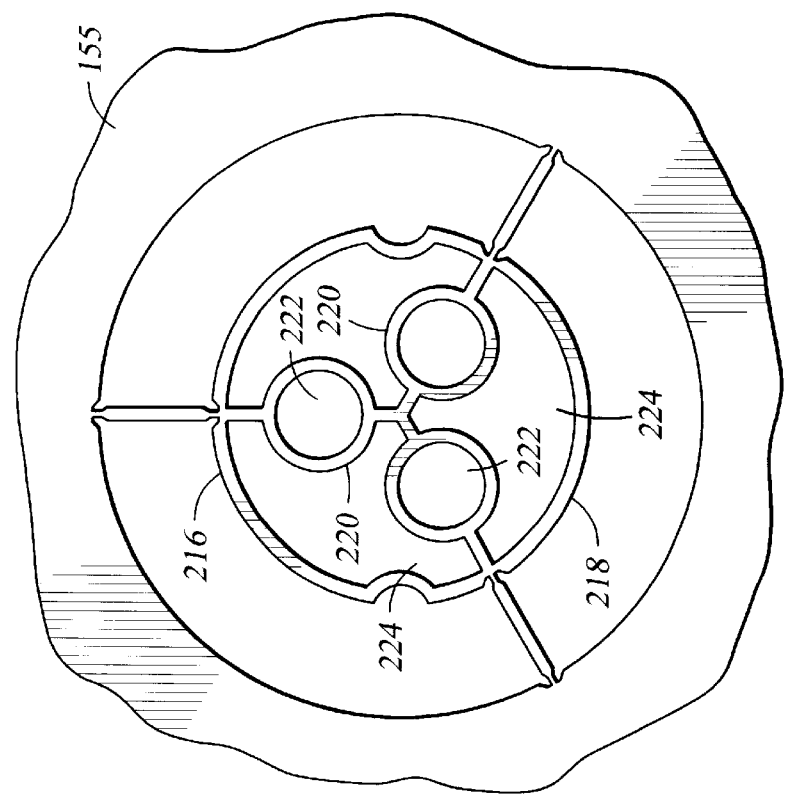
FIG. 27 is an elevational view of a spacer used with the plates shown in FIGS. 24 and 25.

FIG. 27 shows a spacer 216 suitable for use with the plate 212, 212' shown in FIGS. 24 and 25. In addition to an outer ring 218, which is essentially the standard outer profile 159, the spacer 216 is partitioned by three circular partitions 220. The circular partitions 220 enclose three high pressure chambers 222 designed to encompass the high pressure holes 146 arranged in the three round groups in adjacent plates 212, 212'. Between the circular partitions 220 and the outer ring 218 are a plurality of low pressure chambers 224. The low pressure chambers 224 are designed to generally encompass the low pressure holes 148 arranged in a central pattern and an outer annular pattern in the adjacent plates 212, 212'. The circular partitions 220 have a width sufficient to seal the high pressure chambers 222 from the low pressure chambers 224. It can be seen that, after assembly and lamination of the heat exchanger, with spacers 216 between adjacent plates 212 212', the circular partitions 220 isolate the high pressure chambers 222 from the low pressure chambers 224, to create a high pressure passageway and a low pressure passageway through the heat exchanger. As mentioned above, the high pressure passageway in this configuration is in three regions that are substantially parallel with the longitudinal axis of the heat exchanger, while the low pressure passageway has a central region along the axis, and an outer annular region which is substantially coaxial with the high pressure passageway. Therefore, both high pressure and low pressure gas flows substantially axially through the heat exchanger, and heat transfer is substantially transverse to the axis, in this case being both inwardly and outwardly radial from the three regions of the high pressure passageway to the two regions of the low pressure passageway.

Figure 28:
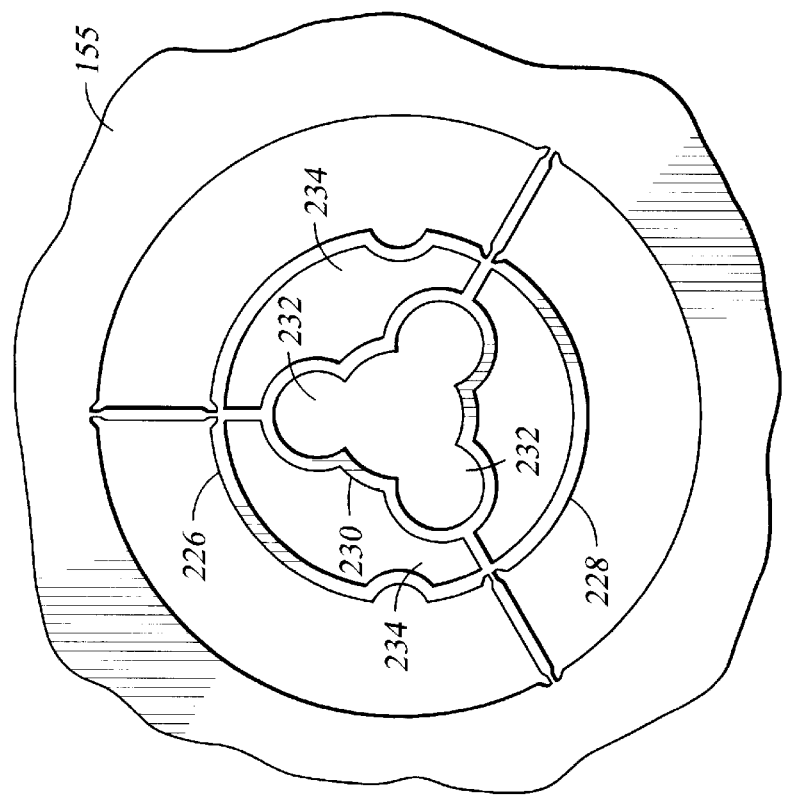
FIG. 28 is an elevational view of an end manifold used with the plates shown in FIGS. 24 and 25.

FIG. 28 shows a manifold 226 suitable for use with the plate 212, 212' shown in FIGS. 24 and 25, and with the end plate 214 shown in FIG. 26. In addition to an outer ring 228, which exhibits the standard outer profile, the manifold 226 is partitioned by an irregular shaped partition 230. The partition 230 encloses a high pressure chamber 232 designed to encompass the high pressure holes 146, and exclude the low pressure holes 148, in end plates 214. Between the partition 230 and the outer ring 228 are a plurality of low pressure chambers 234. The low pressure chambers 234 are designed to generally encompass the low pressure holes 148 in the end plates 214. The partition 230 has a width sufficient to seal the high pressure chamber 232 from the low pressure chambers 234. It can be seen that, after assembly and lamination of the heat exchanger, with spacers 216 between adjacent plates 212, 212', with end plates 214 on each end, and with manifolds 226 outside the end plates 214, the partitions 230 manifold the high pressure passageway to a central location and manifold the low pressure passageway to an outer annular location. This allows connection of the high pressure gas flow to a central inlet port or outlet orifice, at the ends of the heat exchanger, and to connect the low pressure gas flow to an annular inlet or outlet port, as will be discussed below.

Figure 30:
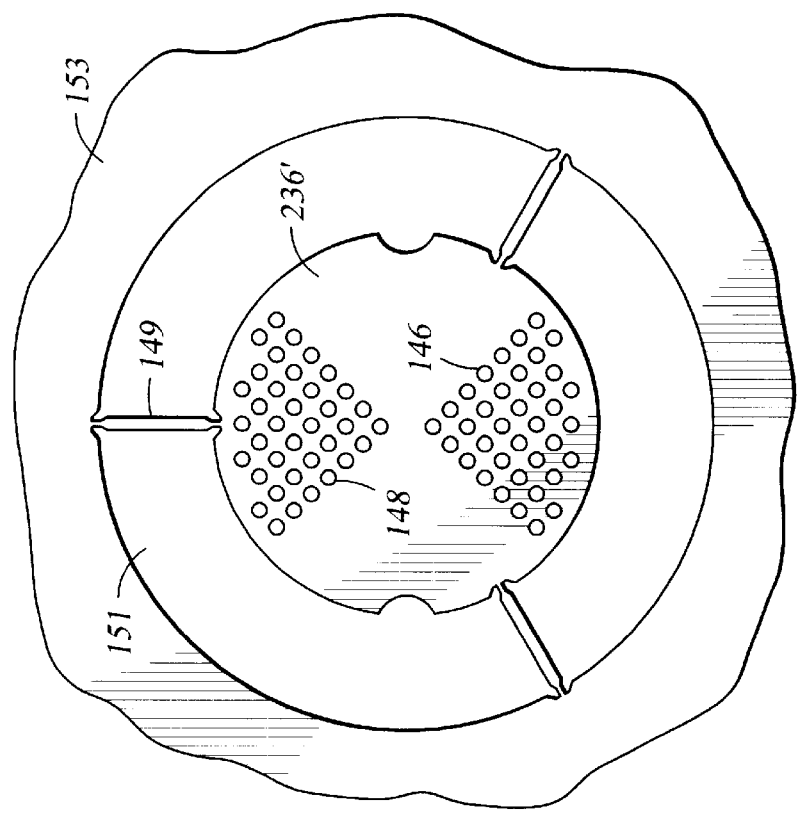
FIGS. 29 and 30 are elevational views of a heat exchanger plate used in a sixth embodiment of the heat exchanger used in the present invention.
Figure 29:
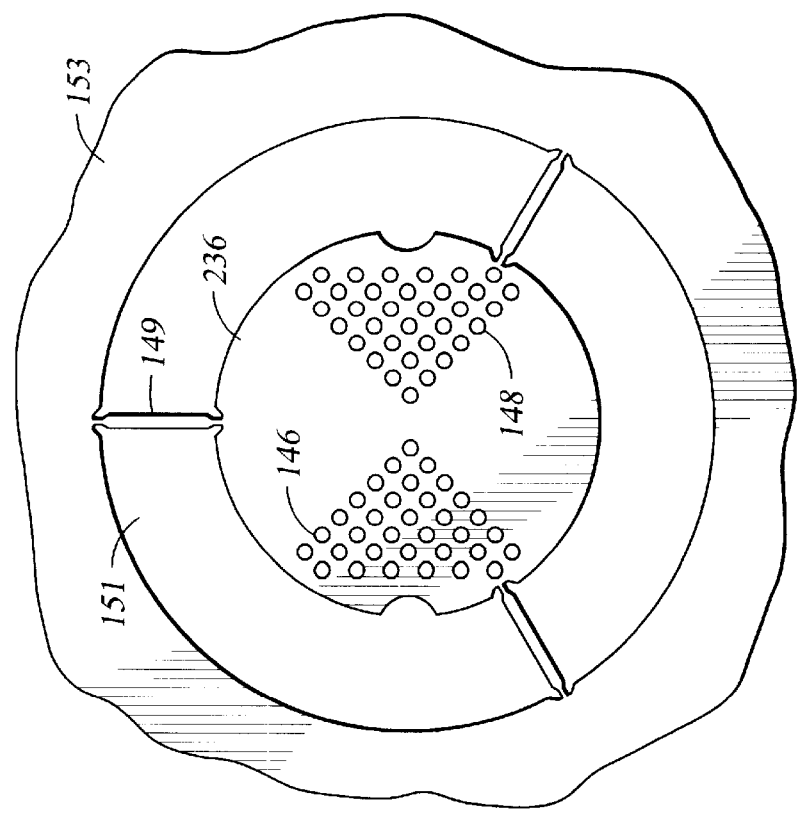

FIGS. 29 and 30 show a sixth configuration of heat exchanger plates 236, 236', which work in a way somewhat similar to the configuration shown in FIGS. 8 and 9. Each plate 236, 236' includes a substantially triangular pattern of high pressure holes 146 to form a high pressure gas passageway. Each plate 236, 236' also includes a substantially triangular pattern of low pressure holes 148, to form a low pressure gas passageway. The patterns of high and low pressure holes are located in different halves of the plate 236, 236'. When first formed from the sheet 153, the plate 236, 236' is supported from the sheet 153 by a plurality of elongate struts 149. A plurality of open voids 151 surround each plate 236, 236', between the plate 236, 236' and the remainder of the sheet 153.

It can be seen that the pattern of high pressure holes 146 in plate 236' is generally rotated 90° from the pattern of high pressure holes 146 in plate 236, with the high pressure holes 146 being on the left as seen in FIG. 29, and at the bottom as seen in FIG. 30. Furthermore, two additional similar plates are used, with one being identical to the plate 236, except having the triangular pattern of high pressure holes 146 at the right, and one being identical to the plate 236', except having the triangular pattern of high pressure holes 146 at the top. Four such plates are laminated adjacently in the final assembly, to cause the high pressure passageway to flow essentially transversely to the axis of the heat exchanger, with flow being in a flat spiral, in this case. This insures that each high pressure hole 146 in the triangular pattern in plate 236 is not aligned with a high pressure hole 146 in the adjacent plate 236'. This relative angular orientation of each of the high pressure patterns on adjacent plates can vary, but it must be sufficient to cause transverse turbulent flow, rather than laminar flow, as high pressure gas flows from plate 236 to the adjacent plate 236', or vice versa.

Similarly, it can be seen that the pattern of low pressure holes 148 in plate 236' is generally rotated 90° from the pattern of low pressure holes 148 in plate 236, with the low pressure holes 148 being on the right as seen in FIG. 29, and at the top as seen in FIG. 30. Furthermore, in the aforementioned two additional similar plates which are used, one is identical to the plate 236, except that it has the triangular pattern of low pressure holes 148 at the left, and one is identical to the plate 236', except that it has the triangular pattern of low pressure holes 148 at the bottom. As a result, the low pressure passageway also flows essentially transversely to the axis of the heat exchanger, with flow again being in a flat spiral. This insures that each low pressure hole 148 in plate 236 is not aligned with a low pressure hole 148 in the adjacent plate 236'. This relative angular orientation of the low pressure patterns on adjacent plates can vary, but it must be sufficient to cause transverse turbulent flow, rather than laminar flow, as low pressure gas flows from plate 236 to the adjacent plate 236', or vice versa.

The transverse, turbulent high pressure gas flow promotes heat transfer from the high pressure gas to the aligned blank quadrant of the adjacent plate 236, 236', which has low pressure gas on its other side, and the transverse, turbulent low pressure gas flow promotes heat transfer from the blank quadrant of the plate 236, 236' to the low pressure gas on the other side.

Figure 32:
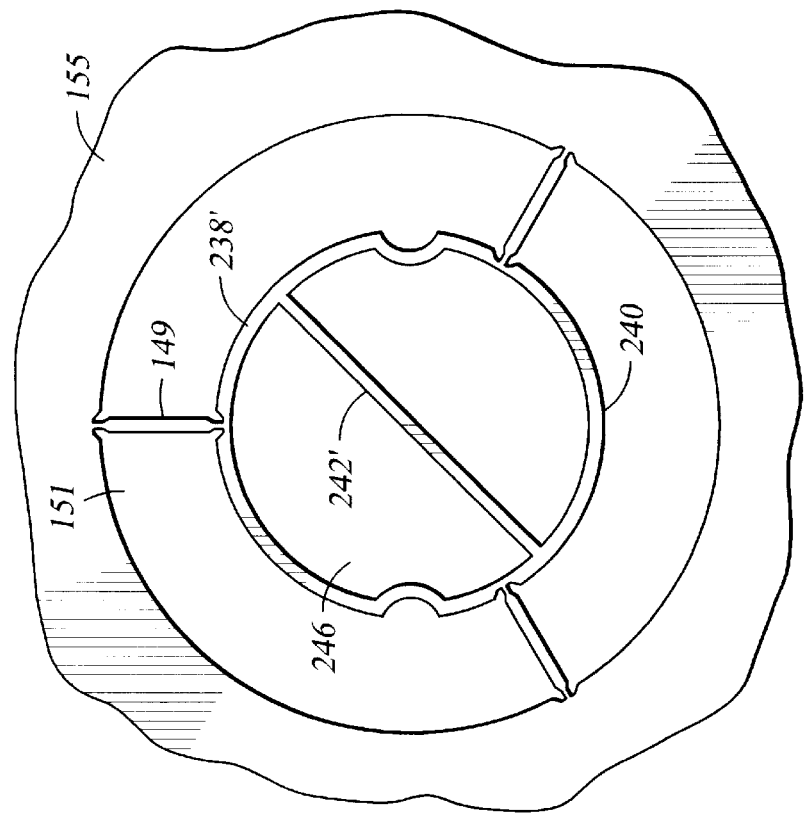
FIGS. 31 and 32 are elevational views of a spacer used with the plates shown in FIGS. 29 and 30.
Figure 31:
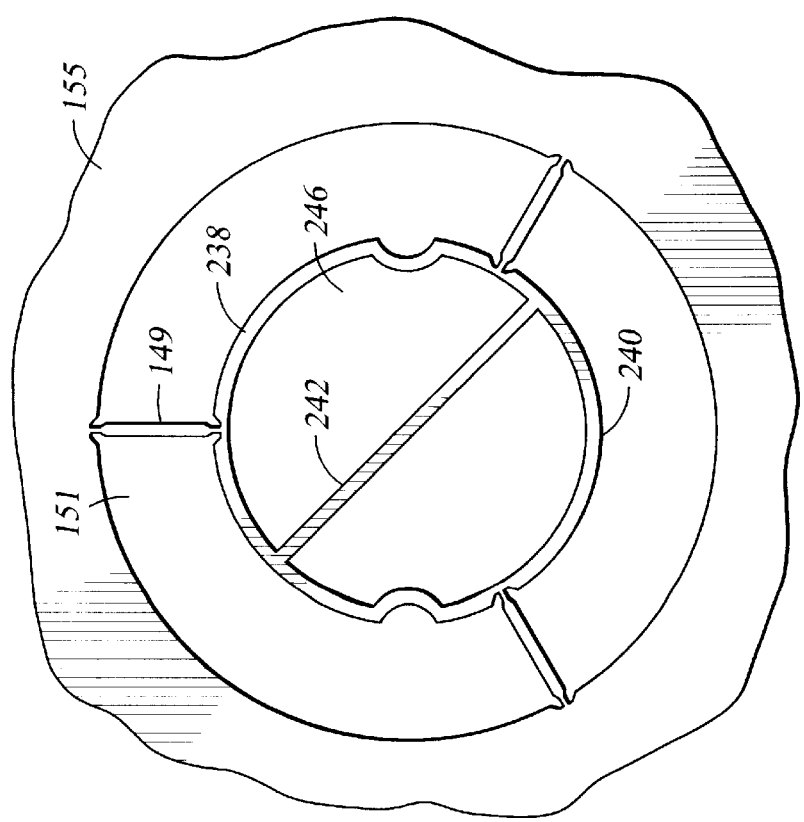

FIGS. 31 and 32 show a spacer 238, 238' suitable for use with the plate 236, 236' shown in FIGS. 29 and 30, along with the two aforementioned additional similar plates, to direct the gas flow in the aforementioned high pressure and low pressure spiral patterns. In addition to an outer ring 240, which exhibits the standard outer profile, the spacer 238, 238' is partitioned by a substantially straight partition 242, 242'. The partition 242, 242' divides a high pressure chamber 244 from a low pressure chamber 246. The spacer 238 is laminated between the plate 236 and the plate 236', and the spacer 238' is laminated between the plate 236' and the first additional plate, which is identical to the plate 236. Finally, another spacer 238 is laminated between the first additional plate and the second additional plate, which is identical to the plate 236'.

The high pressure chamber 244 of spacer 238 encompasses the high pressure pattern of plate 236 and directs high pressure gas flow counterclockwise as seen in the Figures. Similarly, the low pressure chamber 246 of spacer 238 encompasses the low pressure pattern of plate 236 and directs low pressure gas flow counterclockwise as seen in the Figures. Further, the high pressure chamber 244 of spacer 238' encompasses the high pressure pattern of plate 236' and directs high pressure gas flow counterclockwise as seen in the Figures. Similarly, the low pressure chamber 246 of spacer 238' encompasses the low pressure pattern of plate 236' and directs low pressure gas flow counterclockwise as seen in the Figures.

It can be seen that repetition of this series of plates and spacers during assembly and lamination of the heat exchanger, the rotating orientation of the partitions 242, 242' results in flow of the high pressure gas through a spiraling series of high pressure chambers 244, to create a spiraling high pressure passageway through the heat exchanger. Similarly, the rotating orientation of the partitions 242, 242' results in flow of the low pressure gas through a spiraling series of low pressure chambers 246, to create a spiraling low pressure passageway through the heat exchanger. Therefore, both high pressure and low pressure gas flows substantially transversely, in a spiraling pattern, through the heat exchanger, and heat transfer is substantially parallel to the axis, through the blank quadrants of the adjacent plates 236, 236'.

Figure 33:
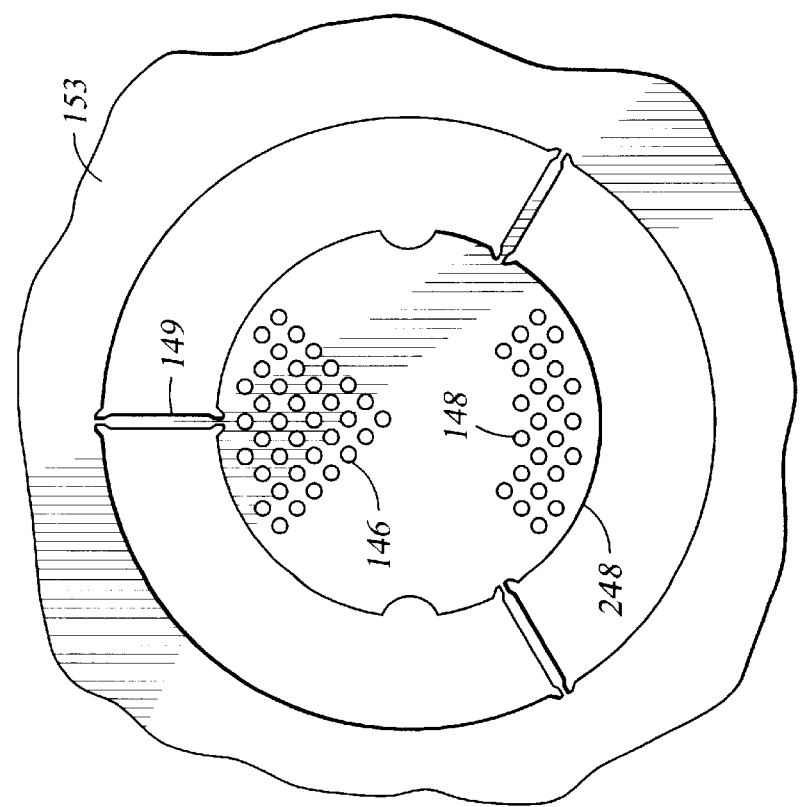
FIG. 33 is an elevational view of an end plate used with the plates shown in FIGS. 29 and 30.

Similarly to several of the other configurations mentioned above, the configuration shown in FIGS. 29 and 30 requires a special end plate to facilitate connection to the two ends of the heat exchanger. FIG. 33 shows such an end plate 248. In the end plate 248, the central portion of the triangular pattern of low pressure holes has been eliminated, to convert it to a partial annular pattern, while the triangular pattern of high pressure holes 146 remains essentially the same as seen in plate 236, 236', shown in FIGS. 29 and 30. Elimination of the central portion of the triangular pattern of low pressure holes 148 from the end plate 248 facilitates the manifolding of the high pressure gas flow to a central inlet port or outlet orifice, and the manifolding of the low pressure gas flow to an annular inlet or outlet port, as will be discussed below.

Figure 34:
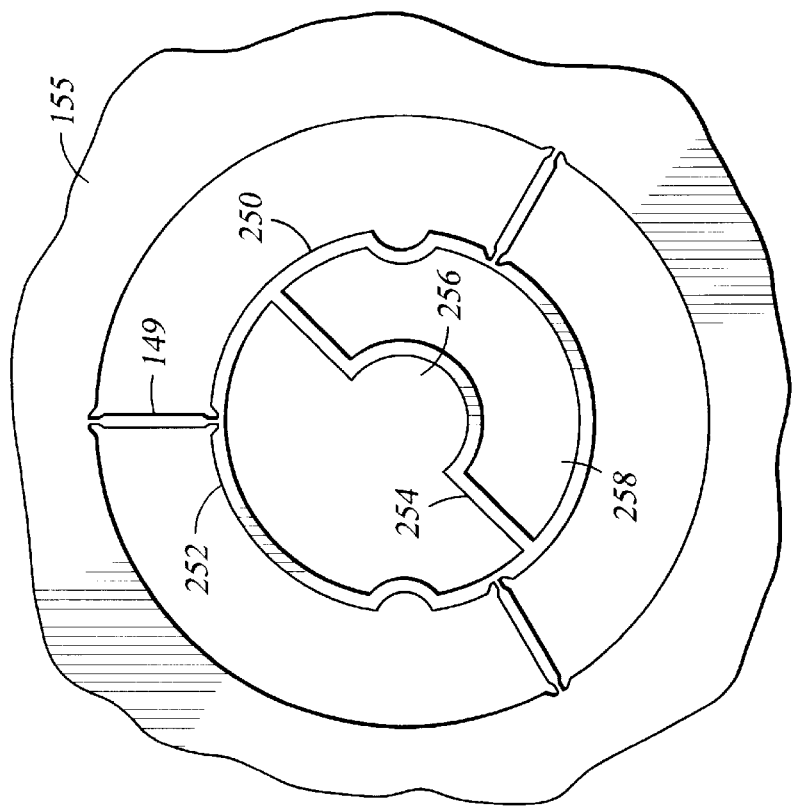
FIG. 34 is an elevational view of an end manifold used with the plates shown in FIGS. 29 and 30.

FIG. 34 shows a manifold 250 suitable for use with the plate 236, 236' shown in FIGS. 29 and 30, and with the end plate 248 shown in FIG. 33. In addition to an outer ring 252, which is essentially the standard outer profile 159, the manifold 250 is partitioned by a semi-circular partition 254. The partition 254 establishes a high pressure chamber 256 designed to encompass the high pressure holes 146, and exclude the low pressure holes 148, in end plates 248. On the other side of the partition 254 is a low pressure chamber 258. The low pressure chamber 258 is designed to generally encompass the low pressure holes 148 in the end plates 248. It can be seen that, after assembly and lamination of the heat exchanger, with spacers 238, 238' between adjacent plates 236, 236', with end plates 248 on each end, and with manifolds 250 outside the end plates 248, the partitions 254 manifold the high pressure passageway to a central location and manifold the low pressure passageway to an outer, partially annular location. This allows connection of the high pressure gas flow to a central inlet port or outlet orifice, at the ends of the heat exchanger, and to connect the low pressure gas flow to an annular inlet or outlet port, as will be discussed below.

Figure 36:
FIG. 36 is an elevational view of a spacer of FIG. 22 superimposed on a plate of FIG. 19 or 20.
Figure 38:
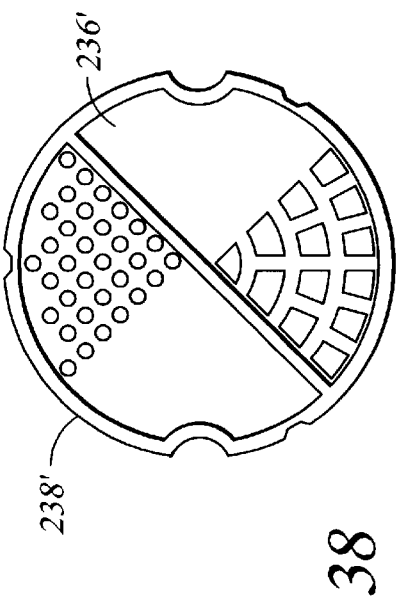
FIG. 38 is an elevational view of a spacer of FIG. 32 superimposed on a plate of FIG. 30.
Figure 35:
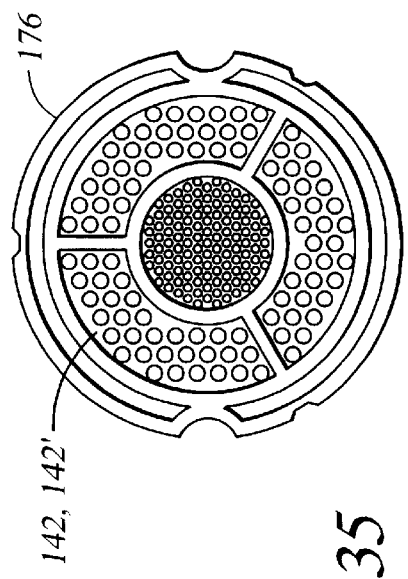
FIG. 35 is an elevational view of a spacer of FIG. 16 superimposed on a plate of FIG. 14 or 15.
Figure 37:
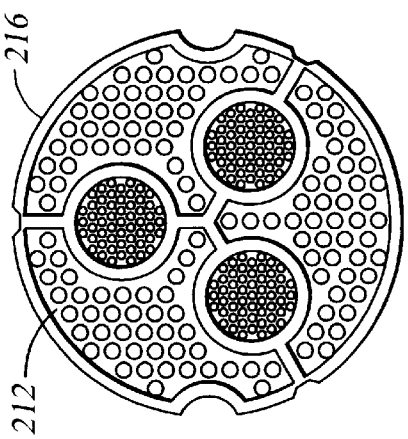
FIG. 37 is an elevational view of a spacer of FIG. 27 superimposed on a plate of FIG. 24 or 25.

To further illustrate, FIG. 35 shows spacer 176 superimposed upon plate 142 or 142'. FIG. 36 shows spacer 190 superimposed upon plate 186 or 186'. FIG. 37 shows spacer 216 superimposed upon plate 212. Finally, FIG. 38 shows spacer 238' superimposed upon plate 236', with an alternative style of high pressure hole.

Figure 39:
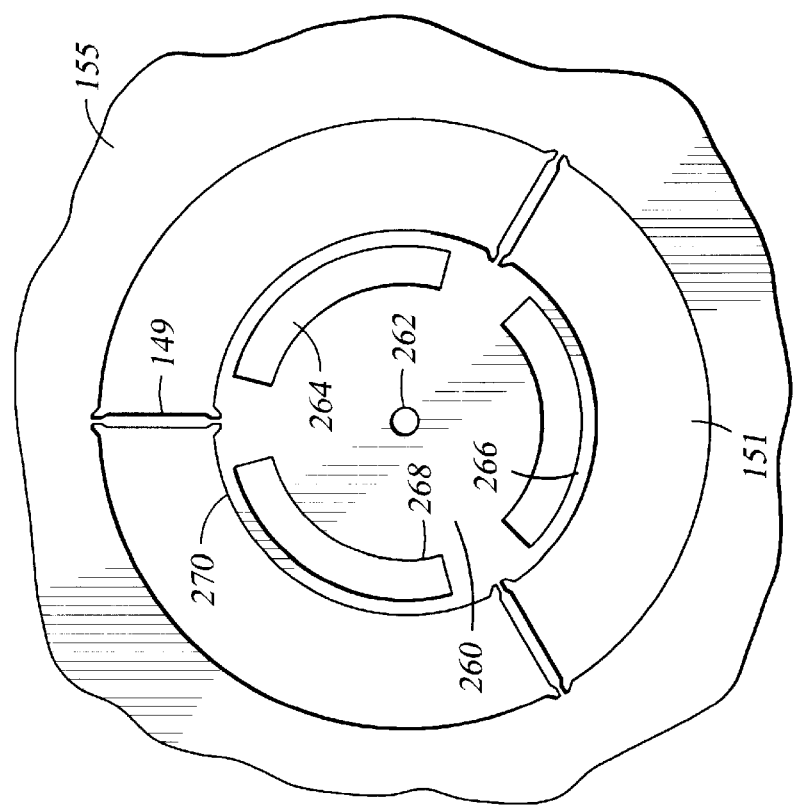
FIG. 39 is an elevational view of an orifice plate which can be used with the heat exchanger plates of FIGS. 14 and 15, 19 and 20, or 24 and 25.

FIG. 39 shows an orifice plate 260 suitable for use with the configurations of heat exchanger plates shown in FIGS. 4 and 5, 14 and 15, 19 and 20, or 24 and 25, in conjunction with the appropriate end plates and manifolds. A central opening 262 can serve as an expansion orifice, with the appropriate diameter. Outer annular openings 264 can serve as inlet low pressure ports, with appropriate outer diameters 266 and inner diameters 268. The outer diameter 270 of the orifice plate 260 aligns with the outer diameter of the heat exchanger plates, spacers, end plates, and manifolds.

Figure 40:
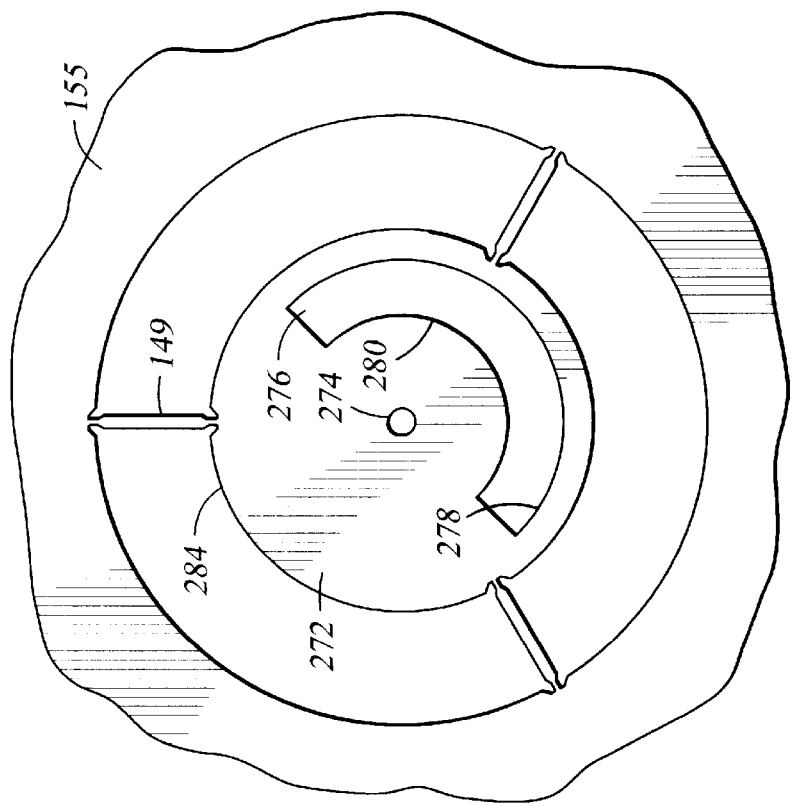
FIG. 40 is an elevational view of an orifice plate which can be used with the heat exchanger plates of FIGS. 29 and 30.

FIG. 40 shows an orifice plate 272 suitable for use with the configurations of heat exchanger plates shown in FIGS. 8 and 9, or 29 and 30, in conjunction with the appropriate end plates and manifolds. A central opening 274 can serve as an expansion orifice, with the appropriate diameter. Outer annular opening 276 can serve as an inlet low pressure port, with appropriate outer diameter 278 and inner diameter 280. The outer diameter 284 of the orifice plate 272 aligns with the outer diameter of the heat exchanger plates, spacers, end plates, and manifolds.

The heat exchanger used in the present invention is a non-planar, specifically cylindrical, micro-miniature heat exchanger. It is made by a photolithography and diffusion bonding process. This allows for the manufacture of the aforementioned multiple designs and intricate patterns which aid in heat exchange. In addition, multiple small heat exchangers can be etched and fabricated at once, providing large quantities of complete units. Further, components needed to connect the high and low pressure gas lines to the heat exchanger can be incorporated into this fabrication process, thereby simplifying construction and increasing precision. Precision construction of the connecting components is vital because of the small size of the heat exchanger, and because of the potential to cause blockage or create leak paths. Finally, the expansion orifice, or impedance component, can be incorporated into this fabrication process, again simplifying construction and making it more precise.

The heat exchanger is essentially a laminated unit of alternating copper plates and stainless steel spacers etched with the appropriate patterns. Etching is carried out by coating the sheets with a thin film of photo-resistive material. This can be applied to the sheets in liquid form, or in the form of a thin solid layer. Art work which incorporates the desired etching pattern is produced, using CAD software. The art work is used to drive a laser photo-tool which reproduces the pattern on the photo-resist coated sheets. This pattern can be produced as a negative image or a positive image. The laser light from the photo-tool combines with the photo-resist coating, and binds the coating to the metal sheets, protecting the coated areas from degradation by etching chemicals known in the art. The sheets are subsequently washed in the etching chemicals which dissolve the unprotected metal and leave the appropriate pattern.

The two limiting factors in the performance of the heat exchanger are the surface area available for heat exchange and the pressure drop experienced as the fluid passes through the heat exchanger. The hole size, number of plates, and outer diameter all effect the pressure drop and surface area. It is important to minimize the pressure drop and maximize the surface area. Using smaller, more numerous holes increases the surface area, but it also increases the pressure drop. For each application, experimentation must be used to finally determine the optimal hole size and pressure drop to maximize cooling power.

Figure 41:
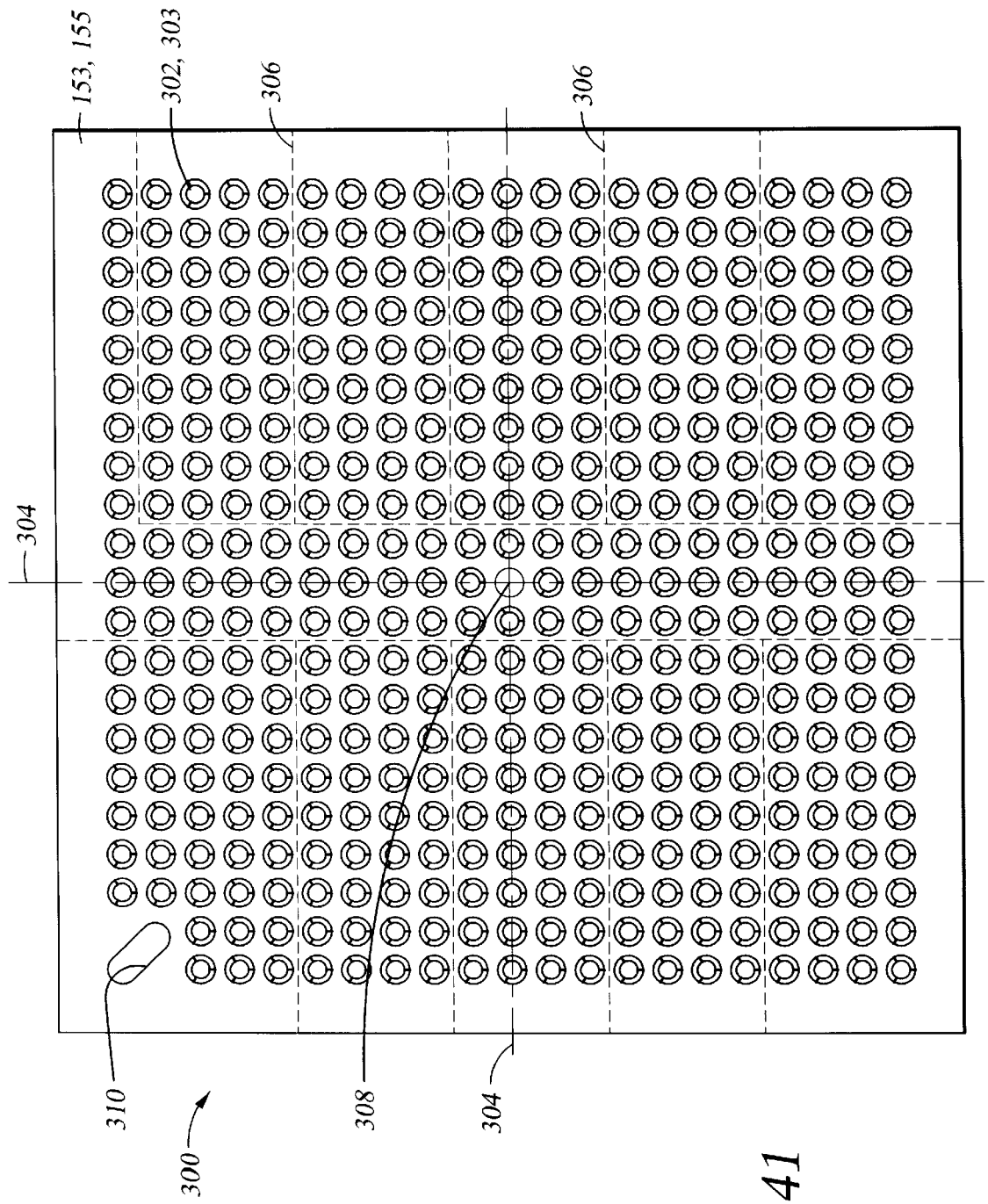
FIG. 41 is an elevational view of a sheet of heat exchanger plates, spacers, end plates, or manifolds, as used in constructing the heat exchanger used in the present invention.

FIG. 41 shows a single sheet or layer 300, which will be laminated to other layers to create a laminated main assembly containing a plurality of laminated subassemblies, with each laminated subassembly constituting a single heat exchanger. After lamination and bonding, the subassemblies are separated from the main assembly. The layer 300 shown can represent a copper sheet 153 of heat exchange plates and end plates, or a stainless steel sheet 155 of spacers and manifolds. For example, to create a heat exchanger appropriate for transluminal ablation of cardiac tissue, heat exchange plates 302, or end plates, with 50 micron high pressure holes and 80 micron low pressure holes are etched into oxygen free copper sheets 153, as shown in FIG. 41, with the sheet 153 being 0.002 inches thick. Each plate 302 maintains its attachment to the sheet 153 via narrow struts 149 extending from the edge of the plate to the sheet 153, as shown in FIG. 14, for example. The struts 149 narrow at their point of attachment to the plate 302 and the sheet 153, to allow easy breaking for removal from the sheet 153. Different hole sizes can be used to optimize the flow of different gas mixtures at different pressures. Hole size and sheet thickness can also be varied to optimize surface area.

In a similar way, spacers, orifice plates, or manifolds 303, are etched onto stainless steel sheets 155. In the final assembly, the spacers 303 separate adjacent copper plates 302 from each other. Similar to the plates 302, the spacers, orifice plates, and manifolds 303 have struts 149 that attach them to the sheet 155. These struts 149 also narrow near the attachment to the spacer 303 or the sheet 155, for easy breakage removal from the sheet 155. Again, a large number of copper plates 302 and spacers 303 can be made from a single sheet 153, 155. Various designs of plates 302 can be etched into a single copper sheet 153, or various designs of spacers, manifolds, end caps, or orifice plates 303 can be etched into a single stainless steel sheet 155. Solid lines 304, or dashed lines 306 illustrate two ways in which the sheet 300 can be divided into segments having differing designs.

In the aforementioned configurations in which the heat exchange occurs radially, some thermal resistance can be overcome by breaking up the high pressure passage and moving it out radially into closer proximity with the low pressure passage. This principle is illustrated in the configurations shown in FIGS. 19, 20, 24, and 25. Because the heat exchanger must be connected to separate high pressure and low pressure lines, a copper end plate and stainless steel manifold must be used at the inlet to some of the heat exchangers. This prevents mixing of high pressure and low pressure gas upon entering and exiting the heat exchanger.

After photo-etching, alternating sheets of stainless steel 155 and copper 153, for example 50 of each, are stacked on top of each other. The sheets 153, 155 are diffusion bonded together, to form a plurality of heat exchangers 0.5 cm to 1.5 cm long, and 0.25 mm in diameter. By alternating sheets of copper plates with sheets of stainless steel spacers, axial heat exchange is reduced while radial heat transfer is promoted. Where required as hereinbefore specified, sheets of copper end plates are positioned at each end of the assembly, with a sheet of stainless steel manifolds on the outside of each sheet of end plates. A sheet of orifice plates is added as the last sheet at one end of the assembly, leaving the sheet of manifolds as the last sheet at the opposite end. A connector for the high and low pressure gas lines can be made by stacking 25 to 50 stainless steel manifolds, with no intervening copper plates.

The sheets 300 are stacked onto ceramic pins, with the ceramic pins aligning two or more sets of alignment holes 308, 310 in the sheets 300, to maintain the desired orientation of the sheets 300, and thereby maintaining precise alignment of each heat exchanger subassembly. The assembly of metal sheets 300 is sandwiched between ceramic plates, which are sandwiched between graphite blocks. The ceramic plates prevent bonding of the metal sheet 300 to the graphite blocks. The graphite blocks evenly distribute weight applied to the ends of the assembly during diffusion bonding.

Diffusion bonding is carried out in a furnace heated to 925° to 1010° C. Once the sheets reach this temperature, it is maintained for between 30 minutes and 2 hours, according to practices known in the art. The plates optionally can be electroplated with an electroless nickel solution prior to assembly, to improve bonding. Weight is added to the top of the assembly during bonding, to create a pressure of 250 psi. to 1000 psi. Variations in temperature and weight can be used to optimize bonding, with lower temperatures requiring more weight, and higher temperatures requiring less weight. In addition, the construction can be vacuumed sealed in a canister and bonded using hot isostatic pressure techniques. Application of a vacuum to the stack also can evacuate the vacuum jacket formed by the annular channels 282, where present, to insure the optimum insulation of the heat exchanger.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

We claim:

1. A miniature cryosurgical system, comprising:
   a compressor for pressurizing a gas mixture;
   a flexible, dual lumen, coaxial catheter, said catheter comprising:

a hollow elongated inner supply tube, said supply tube having a proximal end connected in fluid flow communication with an outlet of said compressor;

a hollow elongated outer return tube, said return tube having a proximal end connected in fluid flow communication with an inlet of said compressor;

a heat exchanger mounted in fluid flow communication with said compressor and said catheter, said heat exchanger comprising:

a high pressure passageway, said high pressure passageway having an inlet port connected in fluid flow communication with said outlet of said compressor, said high pressure passageway having a distal outlet port;

a low pressure passageway, said low pressure passageway lying substantially alongside said high pressure passageway, said low pressure passageway having a distal inlet port, said low pressure passageway having an outlet port connected in fluid flow communication with said inlet of said compressor; and a substantially annular insulating jacket integrally formed within said heat exchanger by formation of substantially annular channels positioned radially outwardly from said high pressure passageway and said low pressure passageway, said annular insulating jacket being evacuated;

wherein the direction of flow from said inlet port to said outlet port of said high pressure passageway is substantially opposite to the direction of flow from said inlet port to said outlet port of said low pressure passageway;

an expansion element mounted within said distal end of said return tube, an inlet of said expansion element being connected in fluid flow communication with said distal outlet port of said high pressure passageway of said heat exchanger, an outlet of said expansion element being connected in fluid flow communication with said at least one distal inlet port of said low pressure passageway of said heat exchanger; and a heat transfer body mounted to said distal end of said return tube adjacent said expansion element, said heat transfer body having an inner surface exposed to said outlet of said expansion element and an outer surface exposed to ambient, for transferring heat from said outer surface of said heat transfer body to said inner surface of said heat transfer body.

2. A miniature cryosurgical system, comprising:

a compressor for pressurizing a gas mixture;

a flexible, dual lumen, coaxial catheter, said catheter comprising:

a hollow elongated inner supply tube, said supply tube having a proximal end connected to an outlet of said compressor;

a hollow elongated outer return tube, said return tube having a proximal end connected to an inlet of said compressor;

a heat exchanger mounted within a distal end of said return tube, said heat exchanger comprising:

a laminated assembly of a plurality of plates of heat conductive material;

a high pressure passageway through said laminated assembly, said high pressure passageway having an inlet port connected to a distal end of said supply tube, said high pressure passageway having a distal outlet port;

a low pressure passageway through said laminated assembly, said low pressure passageway lying substantially alongside said high pressure passageway, said low pressure passageway having a distal inlet port, said low pressure passageway having an outlet port in fluid flow communication with said return tube; and a substantially annular insulating jacket integrally formed within said heat exchanger by formation of substantially annular channels through said plates, said substantially annular channels being positioned radially outwardly from said high pressure passageway and said low pressure passageway, said annular insulating jacket being evacuated;

wherein the direction of flow from said inlet port to said outlet port of said high pressure passageway is substantially opposite to the direction of flow from said inlet port to said outlet port of said low pressure passageway; and wherein each said passageway is arranged to create a tortuous flow path, to ensure turbulent flow of cryogenic gas therethrough;

an expansion element mounted within said distal end of said return tube, an inlet of said expansion element being connected to said distal outlet port of said high pressure passageway of said heat exchanger, an outlet of said expansion element being in fluid flow communication with said at least one distal inlet port of said low pressure passageway; and a heat transfer body mounted to said distal end of said return tube adjacent said expansion element, said heat transfer body having an inner surface exposed to said outlet of said expansion element and an outer surface exposed to ambient, for transferring heat from said outer surface of said heat transfer body to said inner surface of said heat transfer body.

3. A miniature cryosurgical system, comprising:

a compressor for pressurizing a gas mixture;

a flexible, dual lumen, coaxial catheter, said catheter comprising:

a hollow elongated inner supply tube, said supply tube having a proximal end connected to an outlet of said compressor;

a hollow elongated outer return tube, said return tube having a proximal end connected to an inlet of said compressor;

a heat exchanger mounted within a distal end of said return tube, said heat exchanger comprising:

a plurality of plates of heat conductive material laminated in a stack along a longitudinal axis to form an elongate laminated assembly;

a high pressure passageway through said laminated assembly, said high pressure passageway comprising a first plurality of holes through each said plate, said high pressure passageway having an inlet port connected to a distal end of said supply tube, said high pressure passageway having a distal outlet port;

a low pressure passageway through said laminated assembly, said low pressure passageway lying substantially alongside said high pressure passageway, said low pressure passageway comprising a second plurality of holes through each said plate, said low pressure passageway having a distal inlet port, said low pressure passageway having an outlet port in fluid flow communication with said return tube; and a plurality of spacers laminated alternatingly between said plates to form a high pressure flow chamber and a low pressure flow chamber between each pair of adjacent said plates, wherein each said spacer includes a partition dividing said high pressure flow chamber from said low pressure flow chamber;

wherein the direction of flow from said inlet port to said outlet port of said high pressure passageway is substantially opposite to the direction of flow from said inlet port to said outlet port of said low pressure passageway; and wherein each said passageway is arranged to create a tortuous flow path, to ensure turbulent flow of cryogenic gas therethrough;

an expansion element mounted within said distal end of said return tube, an inlet of said expansion element being connected to said distal outlet port of said high pressure passageway of said heat exchanger, an outlet of said expansion element being in fluid flow communication with said at least one distal inlet port of said low pressure passageway; and a heat transfer body mounted to said distal end of said return tube adjacent said expansion element, said heat transfer body having an inner surface exposed to said outlet of said expansion element and an outer surface exposed to ambient, for transferring heat from said outer surface of said heat transfer body to said inner surface of said heat transfer body;

wherein said partitions on said spacers are located to transversely offset adjacent said high pressure flow chambers from each other, and to transversely offset adjacent said low pressure flow chambers from each other, to direct substantial portions of each said passageway substantially transverse to said longitudinal axis of said heat exchanger.

4. A miniature cryosurgical system, comprising:

a compressor for pressurizing a gas mixture;

a flexible, dual lumen, coaxial catheter, said catheter comprising:

a hollow elongated inner supply tube, said supply tube having a proximal end connected to an outlet of said compressor;

a hollow elongated outer return tube, said return tube having a proximal end connected to an inlet of said compressor;

a heat exchanger mounted within a distal end of said return tube, said heat exchanger comprising:

an axially stacked assembly of laminated flat plates and flat spacers, said plates being alternated with said spacers;

a first plurality of holes formed through said plates, forming a passageway for turbulent flow of high pressure cryogenic gas, each said high pressure hole being transversely offset from a corresponding high pressure hole in each adjacent said plate;

a second plurality of holes formed through said plates, forming a passageway for turbulent flow of low pressure cryogenic gas, each said low pressure hole being transversely offset from a corresponding low pressure hole in each adjacent said plate;

a substantially annular channel formed through each said plate and each said spacer to integrally form a substantially annular insulating jacket within said laminated assembly, said substantially annular channel being positioned radially outwardly from said high pressure and low pressure holes, said annular insulating jacket being evacuated;

a plurality of spacers laminated to a first end of said stacked assembly, to create a manifold for connection of high pressure and low pressure gas lines to said heat exchanger; and an end plate laminated to a second end of said stacked assembly, said end plate having an orifice therethrough in flow communication with said high pressure holes;

wherein the direction of flow from said inlet port to said outlet port of said high pressure passageway is substantially opposite to the direction of flow from said inlet port to said outlet port of said low pressure passageway; and a heat transfer body mounted to said distal end of said return tube adjacent said end plate, said heat transfer body having an inner surface exposed to said outlet of said orifice and an outer surface exposed to ambient, for transferring heat from said outer surface of said heat transfer body to said inner surface of said heat transfer body.

* * * * *